United States Patent
Shapanus et al.

[19]

[11] Patent Number: 5,936,715
[45] Date of Patent: Aug. 10, 1999

[54] ON-LINE METHOD AND APPARATUS FOR DETERMINING THE CONDITION OF CIRCULATING FLUIDS

[75] Inventors: Vincent F. Shapanus, Towson; Kevin J. Phipps; Tomislav Posavec, both of Baltimore, all of Md.

[73] Assignee: Art Group, Inc., Towson, Md.

[21] Appl. No.: 08/790,509

[22] Filed: Jan. 29, 1997

[51] Int. Cl.[6] .................................................. G01N 33/28
[52] U.S. Cl. ............................................................. 356/70
[58] Field of Search ................. 356/300, 70, 73, 356/440; 250/226; 324/552–553; 73/19.11, 19.1

[56] References Cited

U.S. PATENT DOCUMENTS

| | | |
|---|---|---|
| 4,757,263 | 7/1988 | Cummings, III et al. .............. 324/552 |
| 4,890,478 | 1/1990 | Claiborne et al. . |
| 4,894,532 | 1/1990 | Peterson et al. ......................... 250/226 |
| 5,521,698 | 5/1996 | Carroll et al. ............................. 356/70 |

*Primary Examiner*—K Hantis
*Attorney, Agent, or Firm*—Reed Smith Shaw & McClay

[57] ABSTRACT

A method and apparatus for determining a condition of a fluid which circulates within a fluid circuit in which the optical characteristics of the fluid change dynamically due to the presence of physical contaminates in the fluid. An optical source is provided for generating light, and an optical detector is provided for receiving the light from the optical source. The fluid is positioned between the optical source and the optical detector. A signal analyzer is coupled to the optical detector. The signal analyzer monitors an output of the optical detector and determines the condition of the fluid in accordance with the output of the optical detector. Such fluid circuits are used in liquid type electrical transformers used for power distribution in the electrical power industry.

22 Claims, 28 Drawing Sheets

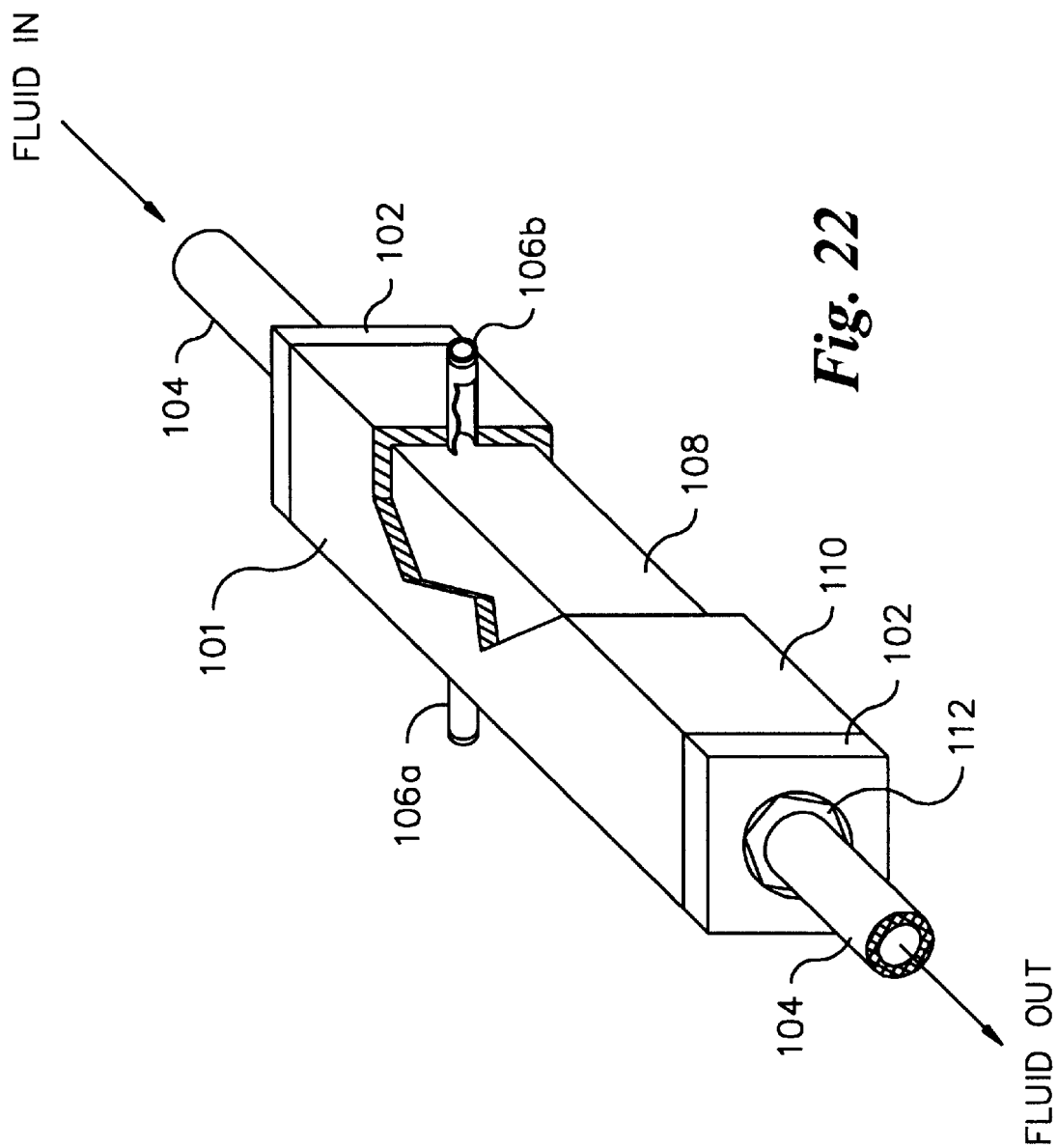

ON-LINE METHOD AND APPARATUS FOR DETERMINING THE CONDITION OF CIRCULATING FLUIDS

FIELD OF THE INVENTION

The present invention relates generally to the field of fluid dynamics. More particularly, the present invention relates to fluids circulating in a closed circuit. Still more particularly, the present invention relates to an on-line system for monitoring fluids in which optical characteristics change dynamically due to the presence of physical contaminates or chemical reactions in which the resulting constituents become dissolved in the fluid.

BACKGROUND OF THE INVENTION

It would be desirable for electrical utilities and other entities which use electrical transformers to have the ability at low cost to monitor the condition of their electrical transformers while such systems are either on-line or when such systems are off-line immediately following a fault condition. The fault condition may be dependent or independent of the transformer being monitored. A variety of techniques have been employed to monitor the condition of transformers in order to evaluate whether or when maintenance should be performed. However, to date such systems lack the ability to continuously monitor the deterioration of liquid insulation (e.g., transformer oil) within electrical transformers at low cost and without efficiency loss.

Currently, there are at least 40 liquid insulation tests for analyzing the condition of electrical transformer oil. These tests typically require extraction of a transformer oil sample from the transformer, followed by analysis (typically in a laboratory) of the extracted oil sample. Some of the analysis techniques include introducing an indicator that reacts with particular substances in the liquid insulation. Since these analysis techniques leave the liquid insulation contaminated with a substance that is not normally in the transformer, the contamination of the fluid makes these test methods unsuitable for an on-line monitoring system.

One on-line system currently in use for monitoring electrical transformers is a gas analysis system. This system monitors specific gases involved in the breakdown of liquid insulation within a transformer. Because gas analysis systems monitor the presence/absence of only a specific limited number of gases, such systems lack the ability to detect substances for which they have not been calibrated. Another deficiency in gas analysis systems is their reliance on filters which separate gases from the liquid insulation. As liquid insulation becomes saturated with particulates during degradation of the insulation, such filters become clogged with these particulates.

Another on-line system currently in use for monitoring electrical transformers uses spectroscopy. This system automatically withdraws a fluid sample from the transformer fluid circuit and performs spectral analysis on the sample. This system requires at least 30 minutes between each sample collection. It is still advisable to perform a more complete gas concentration analysis test after this spectral analysis test or any other on-line test.

Gas analysis tests performed off-line test for Hydrogen, Ethane, Ethylene, Acetylene, Carbon Monoxide and Carbon Dioxide. One interpretation of an abundance of acetylene would indicate an electrical fault. Ethylene is produced by thermal degradation. By interpreting the gas analysis results it may be determined what has occurred in a transformer. One down side of this test is the fact that the transformer must be taken off-line for an oil sample to be withdrawn.

A further method for determining the condition of a transformer is direct visual inspection of the internal components. This method of course requires that the system be taken out of service and opened.

It is therefore an object of the present invention to provide a low cost system for analyzing changes in the optical characteristics of fluids which may be correlated directly to the concentration of chemical constituents or contaminants.

It is a further object of the present invention to provide a system which operates on-line simultaneously while the transformer is either in operation or immediately after a fault condition.

It is a still further object of the present invention to provide a low cost system which can be easily fitted or retrofitted onto existed liquid type electrical transformers in order to continuously analyze the condition of liquid insulation within such transformers.

It is a still further object of the present invention to provide a low cost system for monitoring transformer fluid, which system to continues to function even after the transformer oil becomes a solvent or saturated with particulates.

It is a still further object of the present invention to provide a system which indicates when increased amounts of paper insulation and water particulates are present in transformer oil. It is a still further object to provide such indications independently of external computer processing and telecommunication links.

It is a still further object of the present invention is to provide a system that supplies information to system operators and power plant managers to aid in determining when to place a piece of equipment back in operation following a fault without further test analysis.

These and other objects and advantages of the invention will become more fully apparent from the description and claims which follow or may be learned by the practice of the invention.

SUMMARY OF THE INVENTION

The present invention is directed to a method and apparatus for determining the condition of circulating fluids within a device, such as an electrical transformer, in which the optical characteristics of the circulating fluids may alter dynamically. An optical source is provided for generating light, and an optical detector is provided for receiving the light from the optical source. The fluid is positioned in an optical circuit between the optical source and the optical detector. A signal analyzer is coupled to the optical detector. The signal analyzer monitors an output of the optical detector and measures changes in the condition of the fluid in accordance with the output of the optical detector. This system may be utilized in any closed fluid circuit in which the fluid is normally transparent or translucent in the absence of chemical reactions which result in the fluid becoming a solvent or contaminated by the suspension of particulate matter. The system is particularly applicable to monitoring the insulating fluid of liquid type transformers.

BRIEF DESCRIPTION OF THE DRAWINGS

In order that the manner in which the above-recited and other advantages and objects of the invention are obtained can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

FIG. 22 is a schematic diagram of a fluid module for insertion into a fluid circuit for monitoring the condition of fluid flowing within the fluid circuit, in accordance with an alternative embodiment of the present invention.

DETAILED DESCRIPTION OF THE PREFERRED EMBODIMENTS

Figure 1:
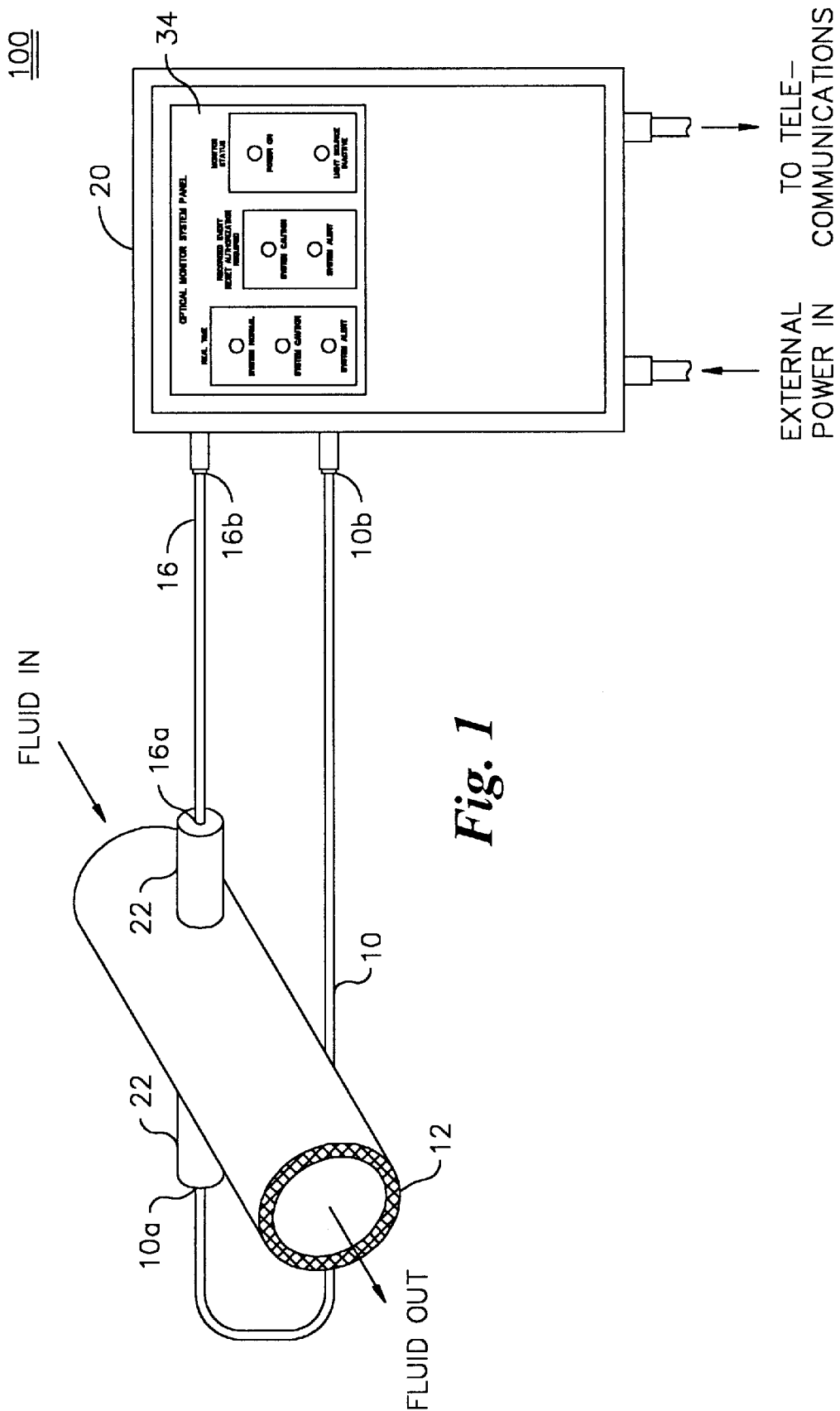
FIG. 1 is a schematic diagram showing the electro-optical components of an on-line system attached to a fluid conduit, for continuously monitoring the condition of a fluid circulating within a fluid circuit, in accordance with a preferred embodiment of the present invention.

Reference will now be made to the drawings wherein like structures are provided with like reference designations. It will be understood that the drawings included herewith only provide diagrammatic representations of the presently preferred structures of the present invention and that structures falling within the scope of the present invention may include structures different than those shown in the drawings.

Figure 2:
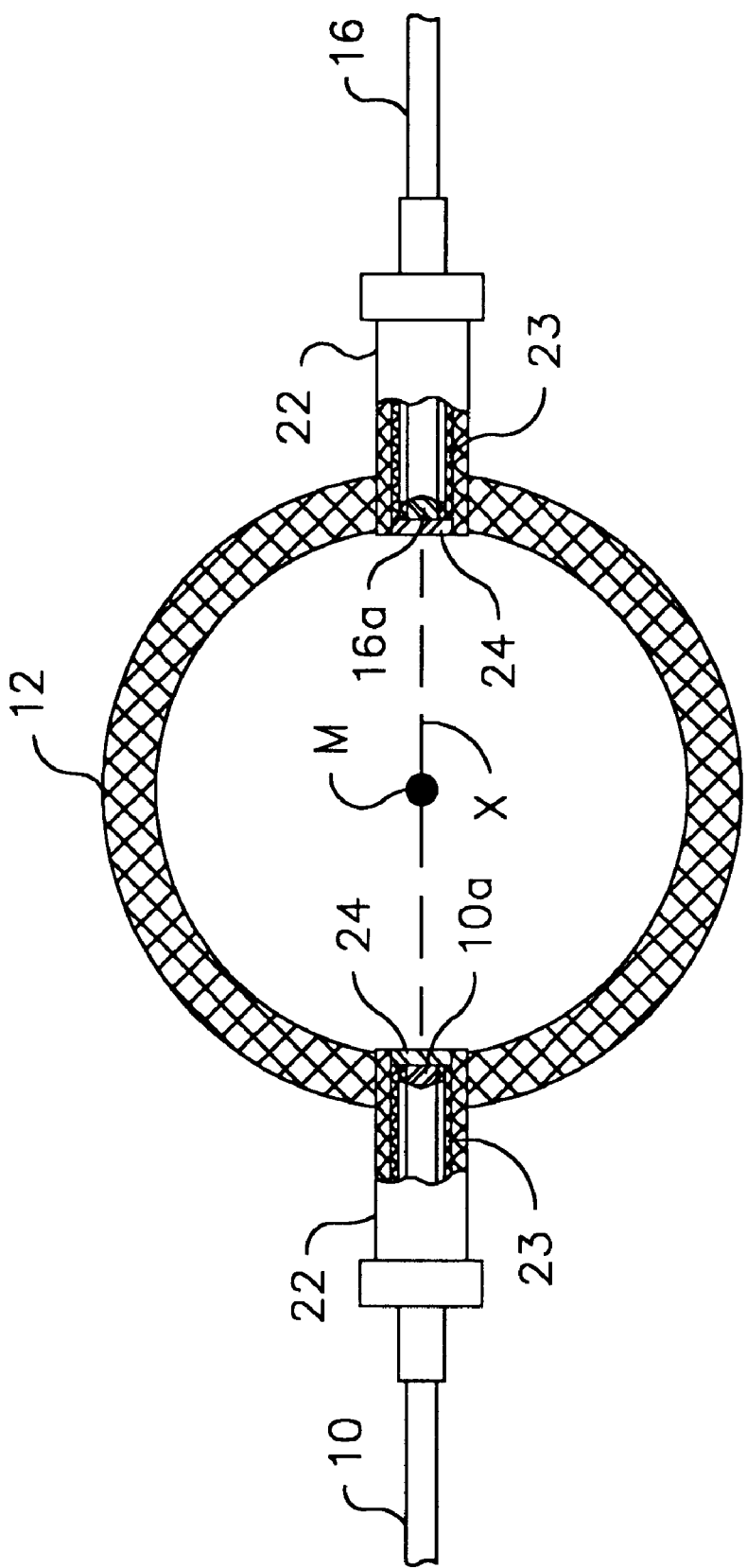
FIG. 2 is a cross sectional cut-away diagram showing an interface for coupling optical fibers for transmitting and acquiring light transmitted through a fluid positioned in a circulation conduit, in accordance with a preferred embodiment of the present invention.
Figure 3:
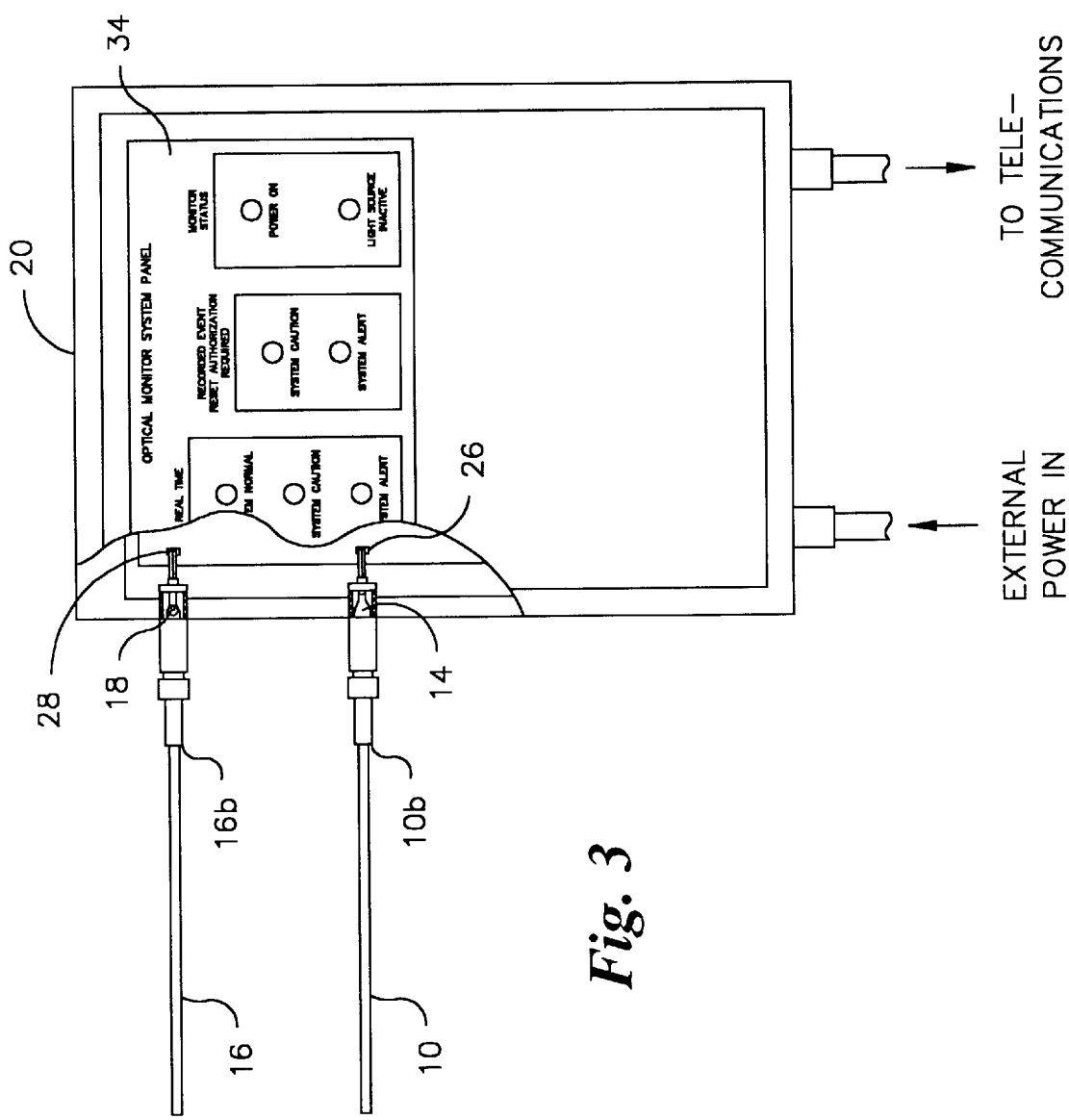
FIG. 3 is a cut-away view showing the optical and electrical connections of the electronics housing illustrated in FIG. 1.

Referring now to FIGS. 1–3, there are shown diagrams illustrating the electro-optical components of an on-line system 100 for continuously monitoring the condition of a fluid (e.g., transformer oil) circulating within a fluid circuit which includes a fluid conduit 12. An optical acquisition device such as an optical fiber strand 10 is optically coupled on its first end 10a to fluid conduit 12 and on its other end 10b to an optical detector 14 (i.e., a photoelectric converter such as a resistive photocell). An optical transmission device such as an optical fiber strand 16 is optically coupled on its first end 16a to fluid conduit 12 and on its other end 16b to an optical source 18. Optical source 18 is preferably an incandescent light source, although it will be understood by those skilled in the art that other light source types such as, for example, a laser of UV light source, may be used. Optical detector 14 and optical source 18 are preferably disposed in a housing 20, which in turn is mounted at an easily accessible location. As shown specifically in FIG. 2, the ends 10a and 16a of the optical fibers are preferably aligned along an axis X which passes through the midpoint M (or central axis) of conduit 12. The ends 10a and 16a are secured along the sides of conduit 12 using optical fiber mounts 22. Each of the ends 10a and 16a terminates within a mount 22 at a clear transparent plate 24. The fiber mounts 22 with optically transmissive tube apertures 24 are mounted opposite each other through the walls of conduit 12 to allow the passage of light through the walls of conduit 12 while still providing a fluid seal. Optical detector 14 and optical source 18 are connected to a circuit board at connections 26 and 28 respectively.

Figure 4:
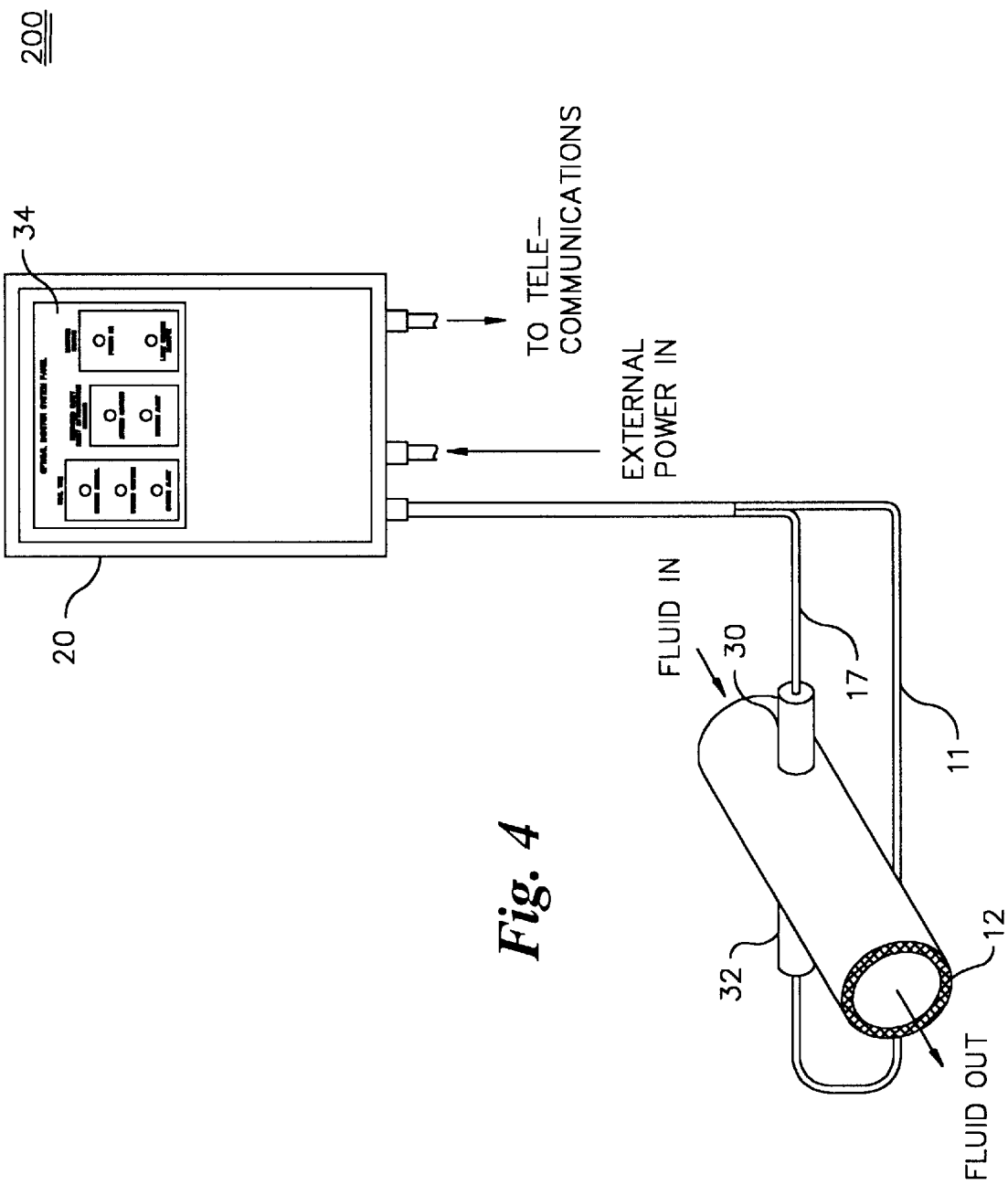
FIG. 4 is a schematic diagram showing the electro-optical components of an on-line system attached to a fluid conduit for continuously monitoring the condition of a fluid circulating within a fluid circuit, in accordance with an alternative preferred embodiment of the present invention.
Figure 5:
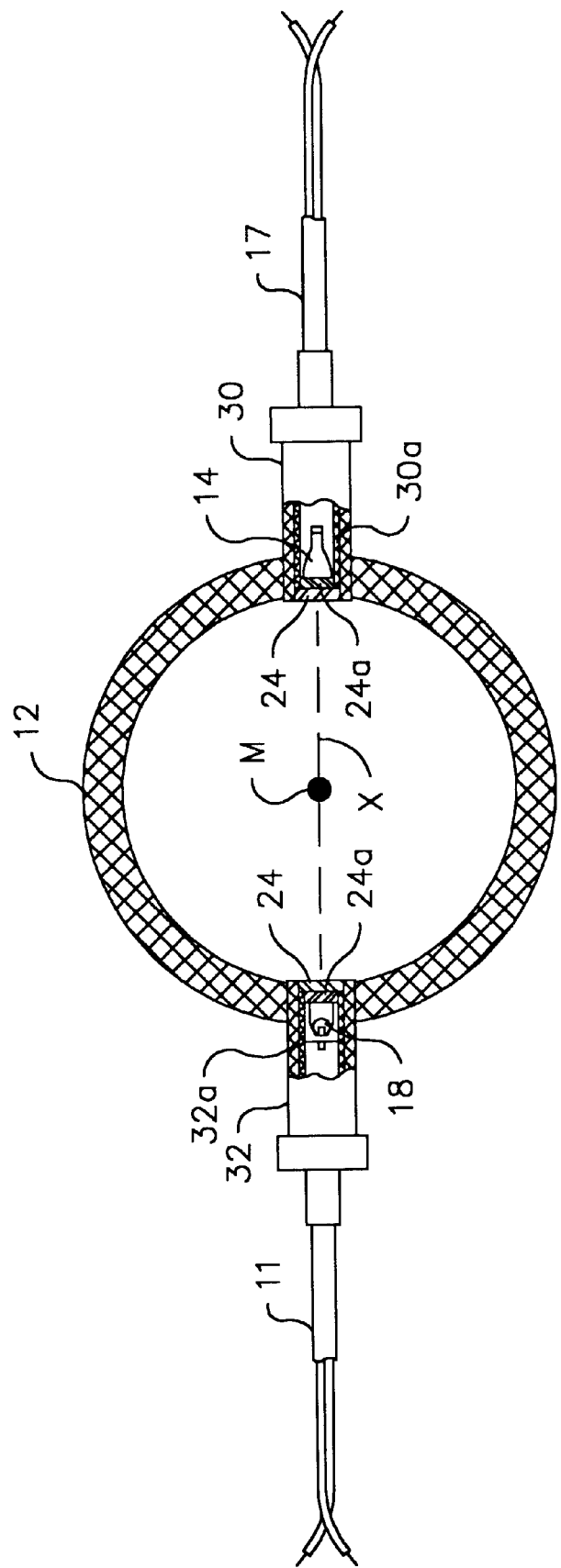
FIG. 5 is a cross sectional cut-away diagram showing an interface for coupling an optical emission source and an optical acquisition device to a fluid circulation pipe, in accordance with a preferred embodiment of the present invention.
Figure 6:
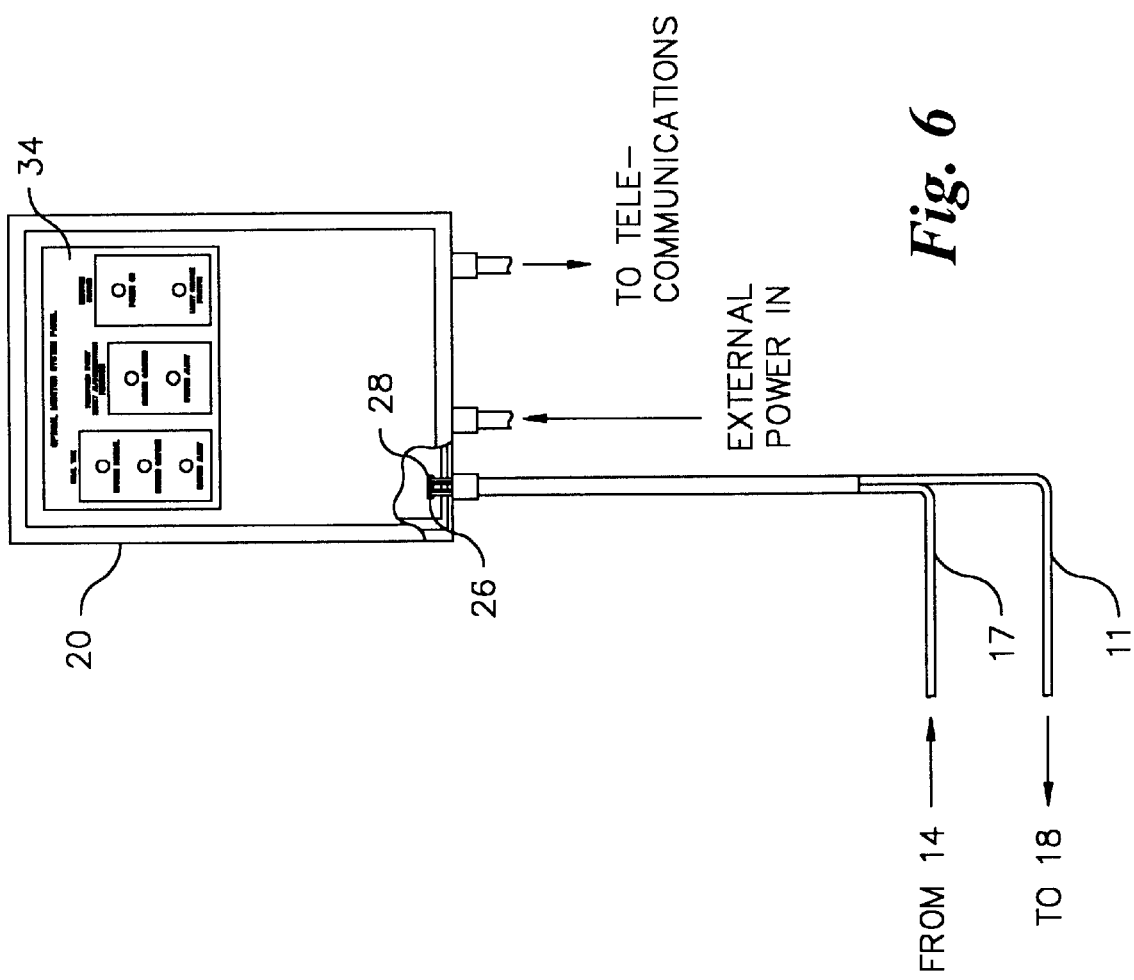
FIG. 6 is a cut-away view showing the electrical connections of the electronics housing illustrated in FIG. 1.

Referring now to FIGS. 4–6, there are shown diagrams illustrating the electro-optical components of an on-line system 200 for continuously monitoring the condition of a fluid (e.g., transformer oil) circulating within a fluid circuit which includes a fluid conduit 12, in accordance with an alternate embodiment of the invention. In system 200, a wire pair 17 is coupled on one end to optical detector 14, and on an opposite end to circuit board connection 26; a wire pair 11 is coupled on one end to optical source 18, and on an opposite end to circuit board connection 28. In system 200, optical detector 14 is disposed within optical detector holder 30a such that the optical reception surface of detector 14 is positioned adjacent to transparent aperture 24a. Optical detector holder 30a is positioned inside of optical detector mount 30. Optical source 18 is similarly disposed within optical source holder 32a such that light emitted from source 18 is transmitted through the transparent aperture 24a positioned adjacent to source 18. Optical source 18 and optical detector 14 are aligned along an axis X which passes through the midpoint M of tube 12. Both mounts 30a, 32a are sealed with optically transmissive tube apertures 24.

Figure 7:
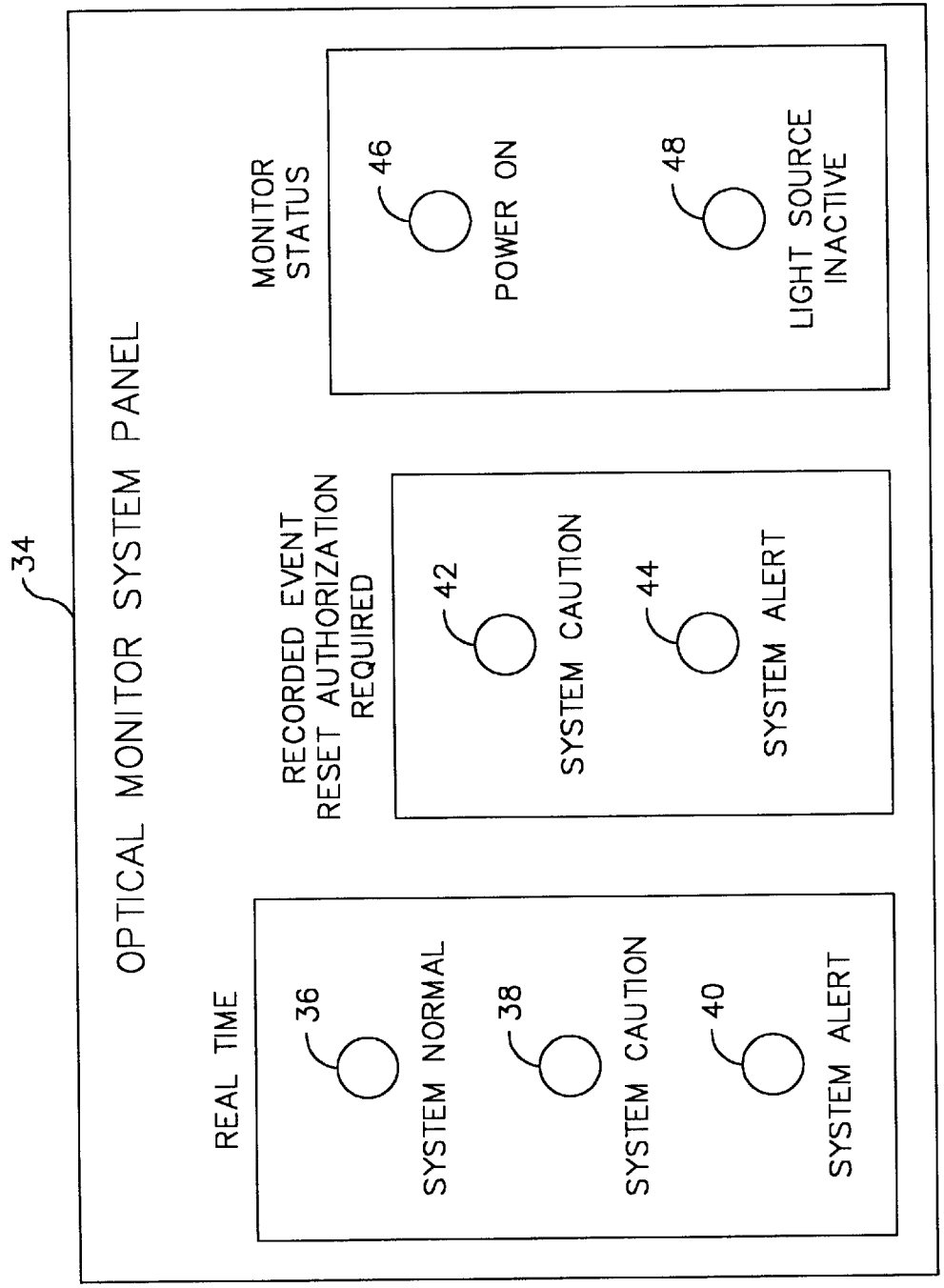
FIG. 7 is a front view of an optical monitoring system indicator panel showing the geometrical layout and labeling of the light indicators.

Referring now to FIG. 7, there is shown a front view of an optical monitoring system indicator panel 34, in accordance with a preferred embodiment of the present invention. The display panel 34 has three primary LED's, two secondary LED's and two system indicator LED's. The first primary LED 36 is green, the second primary LED 38 is yellow, and the third primary LED 40 is red. When the condition of fluid in conduit 12 is normal, the green LED 36 is illuminated. However, as the condition of the fluid degrades, less light from source 14 is transmitted through the fluid located between the clear transmissive plates 24 and the voltage drop across the detector 14 increases. When the voltage drop across the photoelectric detector 14 passes a first of two reference voltages, this triggers a signal analyzer 50 to switch on the yellow LED 38 of the display panel 34. Also at this time, a secondary yellow LED 42 is switched on and latched to remain on regardless of the fluid condition until a reset switch is applied. As the fluid continues to degrade further, still less light is transmitted from source 14 through the fluid between the clear transmissive plates 24 and the voltage drop across the photoelectric converter 14 increases still further. When the voltage drop across the photoelectric detector 14 passes the second reference voltage, this in turn triggers the signal analyzer 50 to illuminate the red LED 40. Again at this time, a secondary red LED 44 is illuminated and latched on until a reset switch is applied. The purpose for the latched LED's 42 and 44 is to record the event of passing a reference voltage for later inspection by service personnel. When the present invention is used to monitor the condition of oil circulating within an electrical transformer, the second reference voltage preferably corresponds to the percentage of light which passes through a sample of oil which contains the maximum allowable concentrations of all relevant dissolved gases or contaminants. The first reference voltage preferably corresponds to the percentage of light which passes through a sample of oil which contains the maximum allowable concentration of one dissolved gas concentration or some combination of dissolved gases or contaminants. See IEEE Guide for the Detection of Generated Gases in Oil-Immersed Transformers and their Relation to the Serviceability of the Equipment, ANSI/IEEE C57.104-1978, approved Jun. 7, 1978. In an alternative embodiment, the first reference voltage preferably corresponds to a situation where the dielectric strength of the transformer oil has not significantly changed from its initial clean state, and represents a condition when the insulation oil contains sufficient particles to indicate that maintenance should be scheduled for the transformer. The second reference voltage is preferably used to indicate when the particle density suspended in the oil insulation has increased to the point when a definite drop in dielectric strength has occurred, and represents a condition when the insulation oil contains sufficient particles to indicate that the transformer should be immediately shut down. The present invention can of course be calibrated to detect other conditions by adjustment of the reference voltages used to trigger the LED's described above. By choosing the conditions of most concern for industry, the instrument can be calibrated for those conditions.

Although only two reference voltages are used in the system described above, it will be understood by those skilled in the art that additional reference voltages and LED's can easily be added. The two system indicators on the display panel 34 are a green power indicator LED 46 and a red light source indicator LED 48. When power is applied to the system the green power indicator LED 46 is illuminated. If the optical source 18 should fail, the red light source indicator LED 48 is illuminated.

Figure 8:
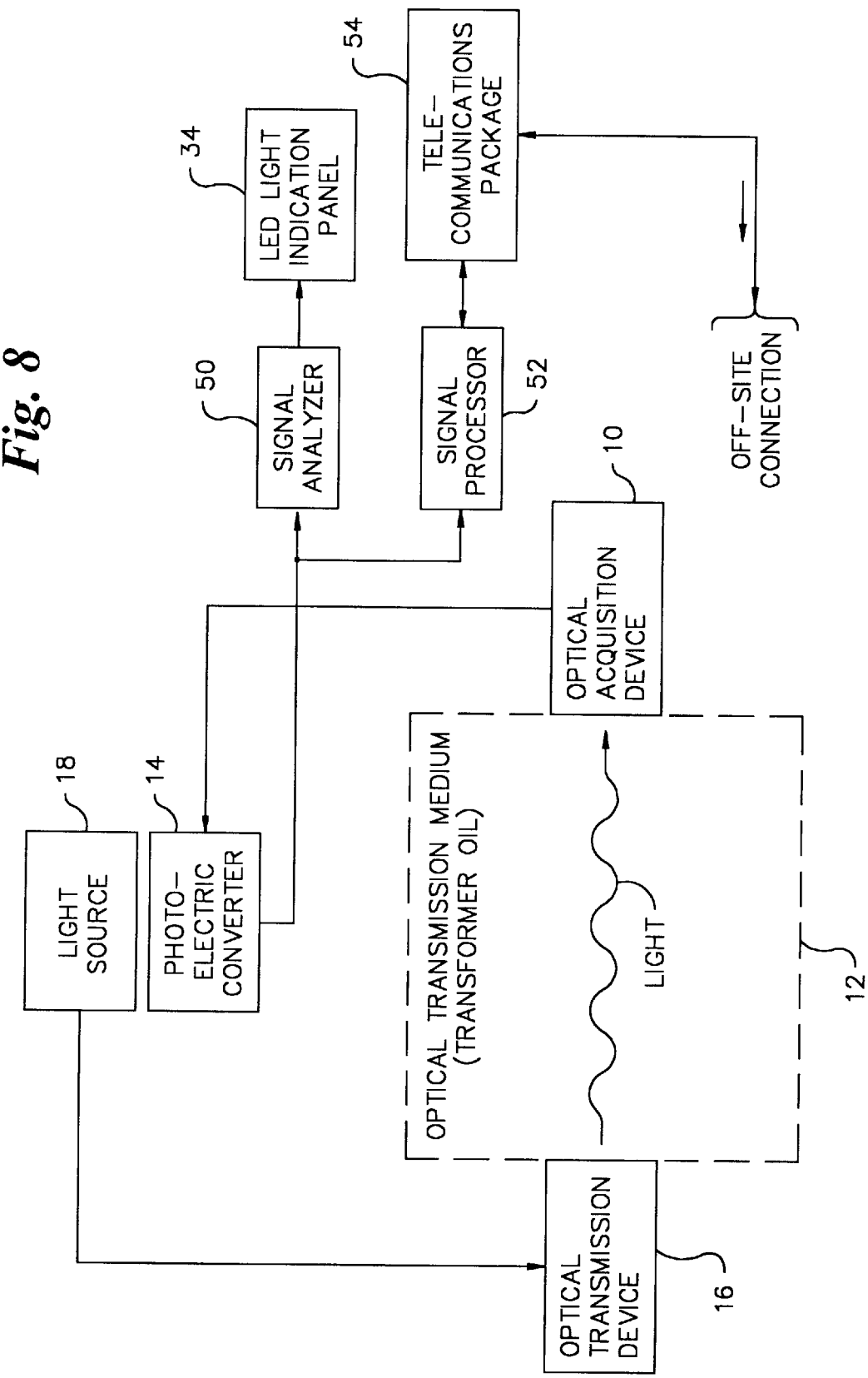
FIG. 8 is a functional block diagram showing the operation of a fluid monitoring system in accordance with a preferred embodiment of the present invention.
Figure 9:
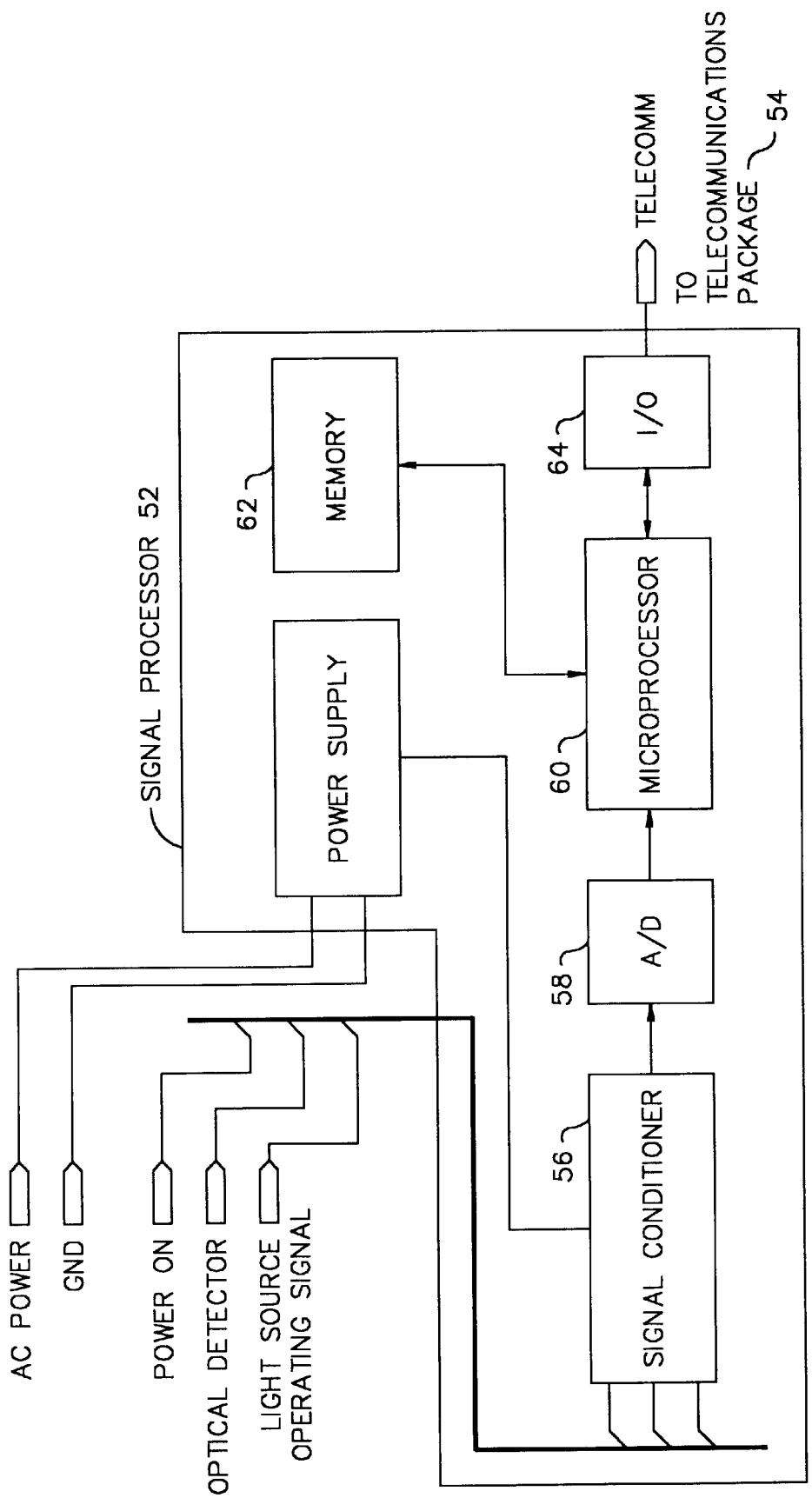
FIG. 9 is a block diagram illustrating the implementation of a signal processor in accordance with the present invention.

Referring now to FIG. 8, there is shown a functional block diagram illustrating the operation of a system for monitoring the condition of a circulating fluid, such as transformer oil, in accordance with a preferred embodiment of the present invention. The system illustrated in FIG. 8 can be used to monitor a device such as an electrical transformer either while the device is on-line and operating or immediately after a fault condition occurs in the device. During operation of the system, light emitted from light source 18 is directed to and aimed through fluid positioned within the interior of conduit 12. A portion of this light is received by the detector 14. The portion of light received by the detector 14 depends on the concentration of any dissolved gases or contaminants in the fluid. In hazardous environments, e.g., high temperature fluids, fiber optics 10 and 16 are preferably positioned between conduit 12 and detector 14 and source 18, as shown in FIG. 1. A signal analyzer 50 is coupled to the output of the photoelectric converter 14. The signal analyzer 50 determines the condition of the fluid circulating within a device by evaluating the intensity of the light received by detector 14. More particularly, based on the intensity of the light received by converter 14, the signal analyzer 50 determines whether a system alert or a system caution indication should be given. The output of the signal analyzer 50 is coupled to a light indication panel 34 which include lights that are selectively illuminated based on the output of signal analyzer 50. In a preferred embodiment, the output of photoelectric converter 14 is also coupled through a signal processor 52 to a telecommunications package 54, which functions to transmit the output of photoelectric converter 14 to a remote monitoring site (not shown). Through the use of telecommunications package 54, a central monitoring location may be employed to continuously monitor multiple devices (e.g., transformers). Telecommunications package 54 may take several forms including, for example, land line telephone communication links, cellular telephone links, fiber optic links or microwave or radiowave links between a device to be monitored and a central remote monitoring station. As shown in FIG. 9, signal processor 52 may consist of standard components such as signal conditioner 56, analog to digital converter 58, microprocessor 60, memory storage device 62, and an input and output device 64.

Figure 10:
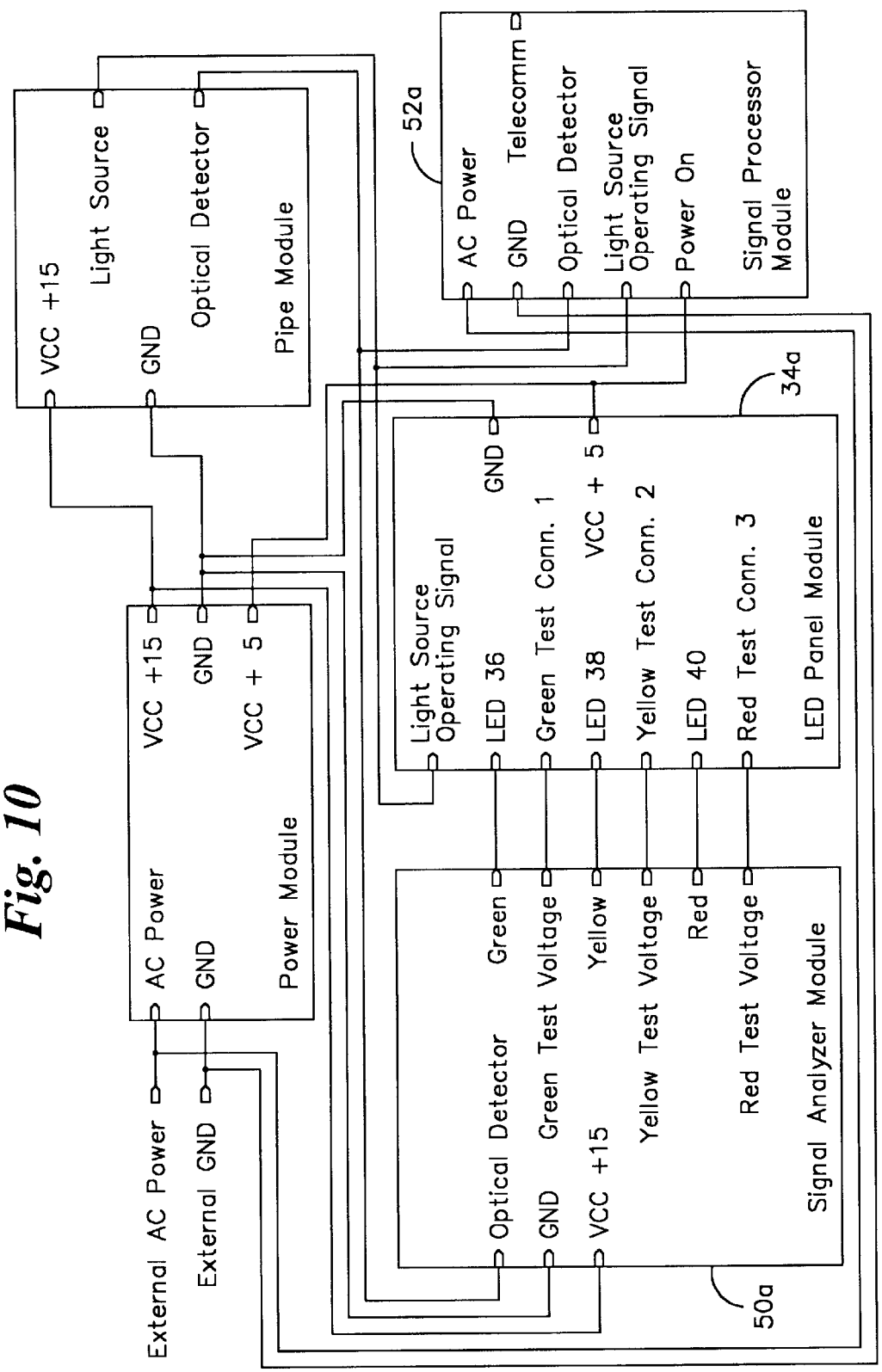
FIG. 10 is a functional block diagram showing the architecture of the electronics used for implementing a preferred embodiment of the present invention.
Figure 11:
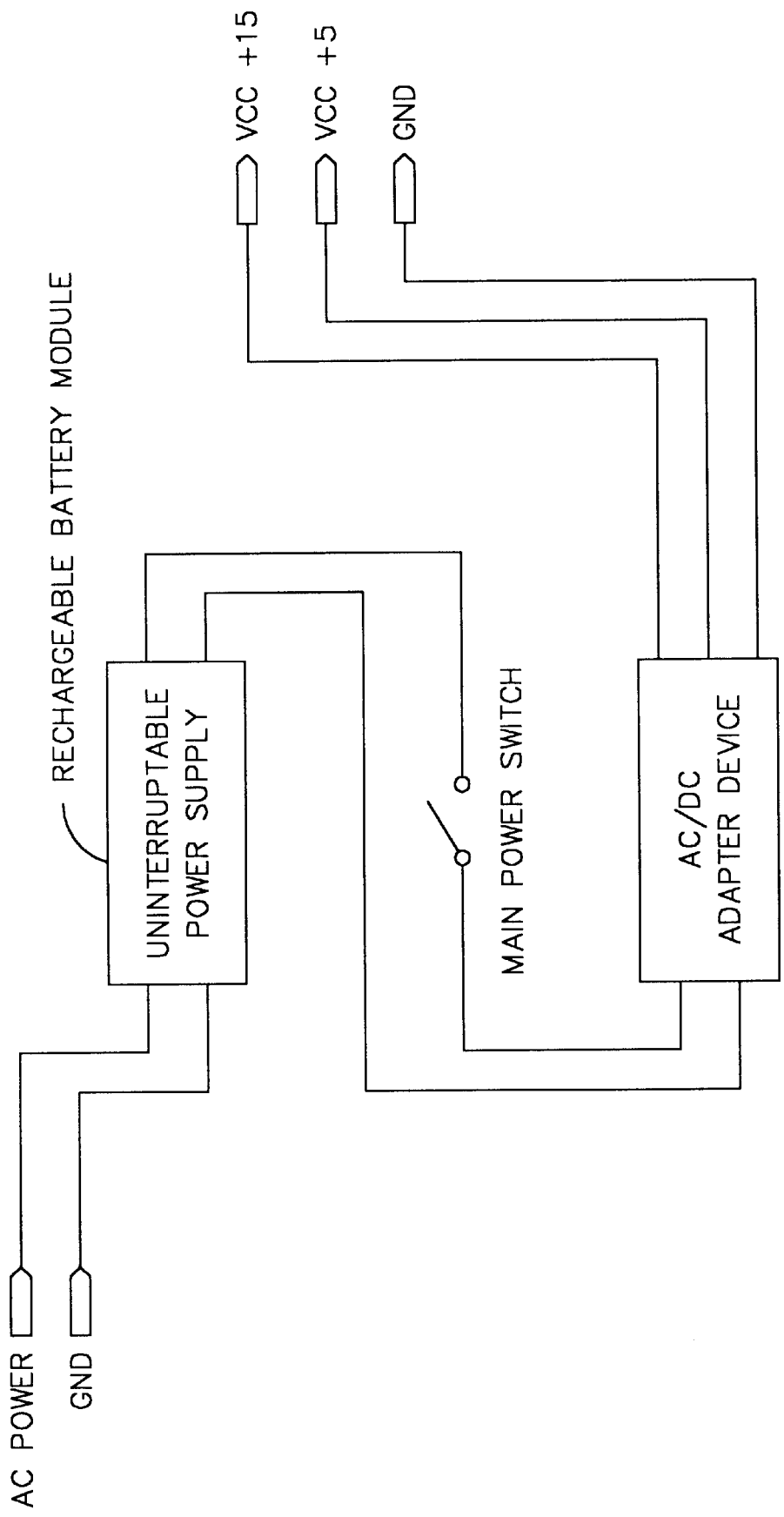
FIG. 11 is a circuit diagram illustrating an exemplary circuit for implementing a power module in accordance with the present invention.
Figure 12:
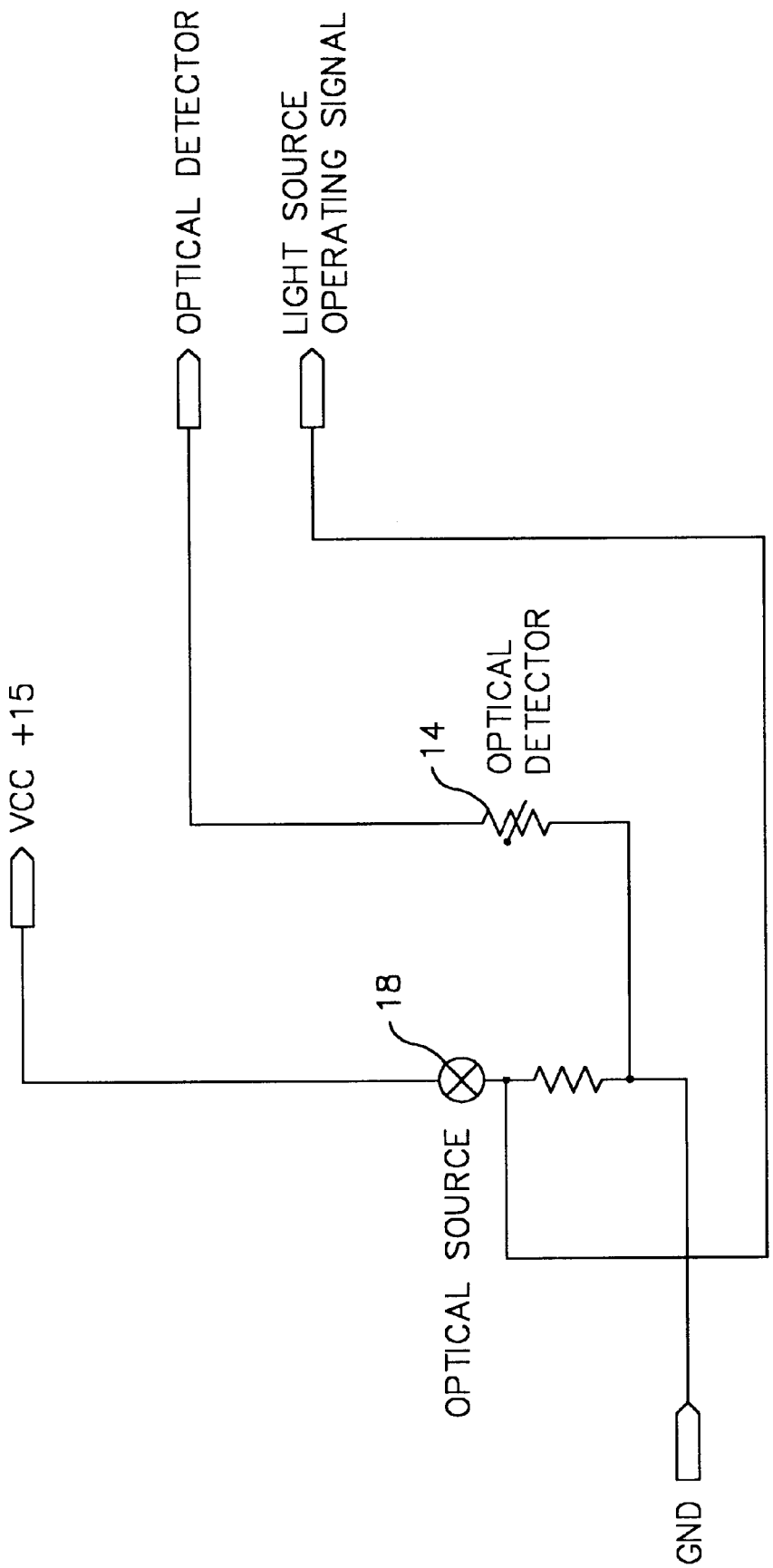
FIG. 12 is a circuit diagram illustrating an exemplary circuit for implementing a detection module in accordance with the present invention.

Referring now to FIG. 10, there is shown a functional block diagram illustrating the architecture of the electronics used for implementing the present invention. The system shown in FIG. 10 includes a power module which accepts an ac power input and supplies two dc voltages (i.e., +5 v and +15 v) as its outputs, and a pipe module which accepts as its input a dc voltage and supplies a light source operating signal and an optical detector signal as its outputs. The light source operating signal is used for monitoring whether the light source is inactive (e.g., inoperable) and controls the state of LED 48 on panel 34, and the optical detector signal provides a voltage representative of the intensity of light received by detector 14 to signal analyzer module 50a and signal processor module 52a. The signal analyzer module 50a (shown in further detail in FIG. 13) accepts as its inputs a dc voltage and the optical detector signal, and supplies as its outputs a green signal for controlling the state of LED 36, a yellow signal for controlling the state of LED 38, a red signal for controlling the state of LED 40, and three test voltages i.e., green, yellow and red test voltages) which are preferably used for calibrating the circuitry in the signal analyzer module 50a. The LED panel module 34a accepts as its inputs the output voltages supplied by module 50a, the light operating signal from the pipe module, and a dc supply voltage, and module 34a uses these inputs to control the states of the LEDs on panel 34. The structure of the power and pipe module are shown in further detail in FIGS. 11 and 12, respectively.

Figure 13:
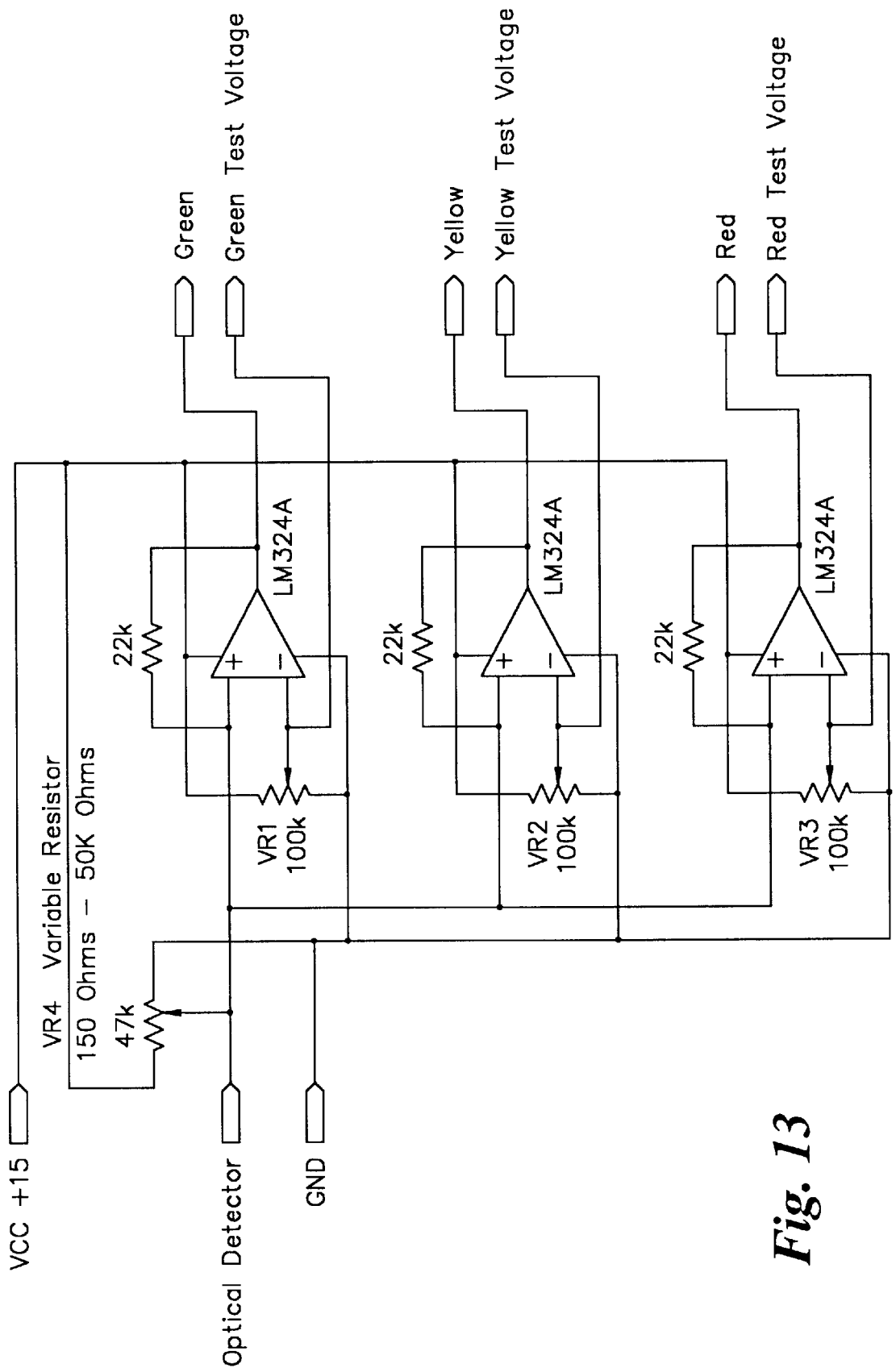
FIG. 13 is a circuit diagram illustrating an exemplary circuit for implementing a signal analyzer in accordance with the present invention.
Figure 14:
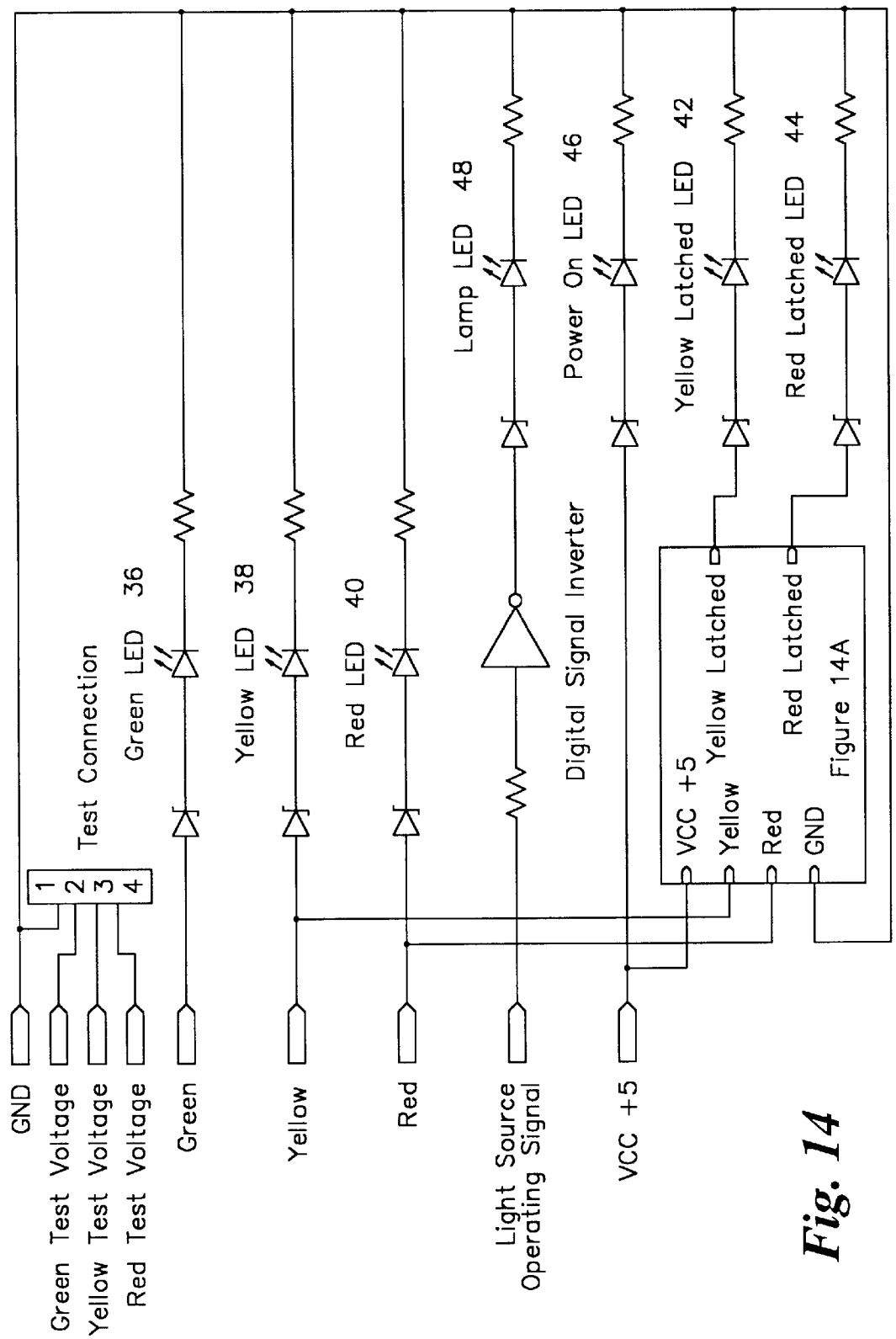
FIG. 14 is a circuit diagram illustrating an exemplary circuit for implementing a display panel with test ports in accordance with the present invention.
Figure 14A:
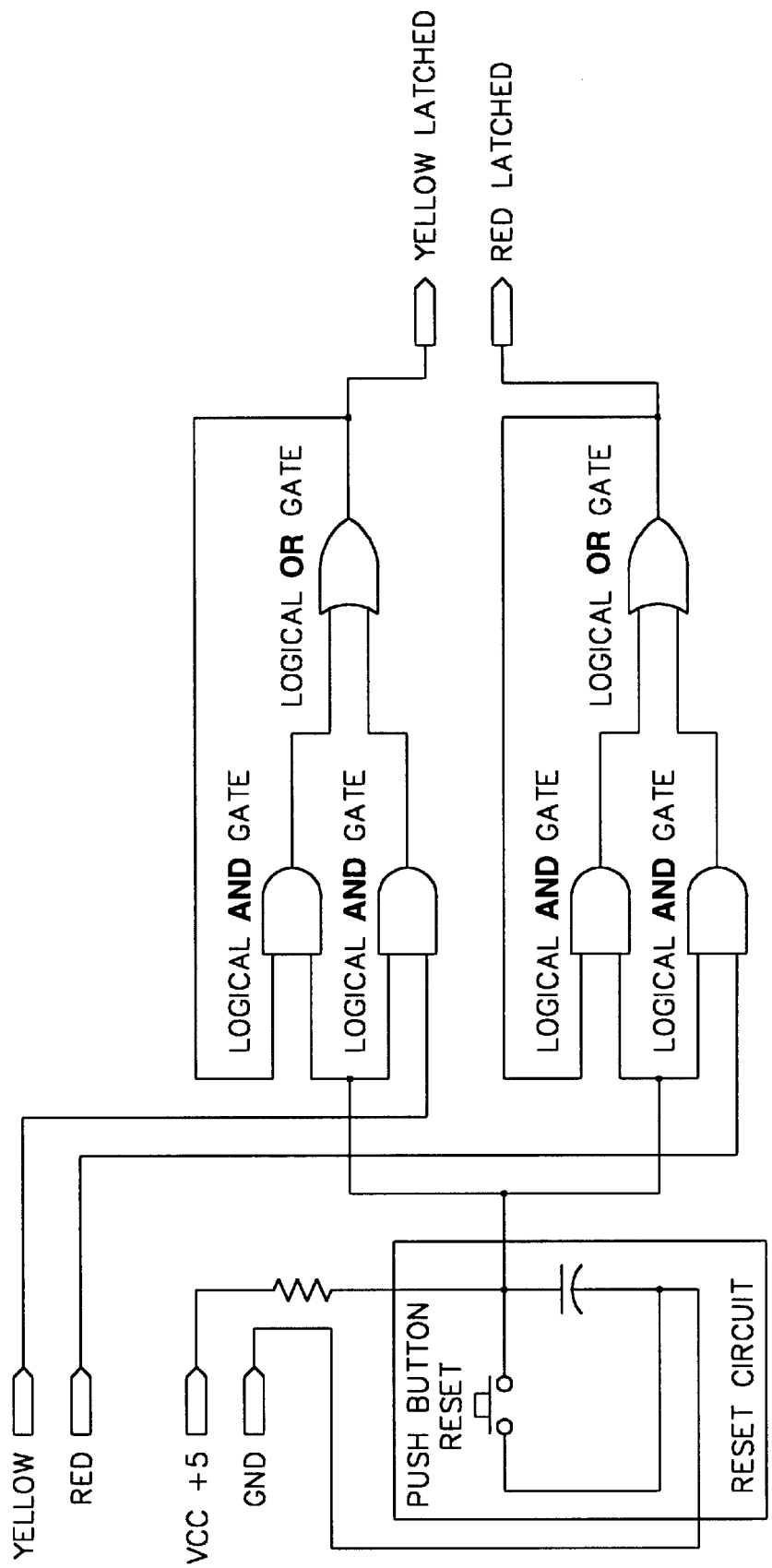
FIG. 14A is a circuit diagram illustrating an exemplary circuit for implementing a latching circuit for the display panel in accordance with the present invention.

Referring now to FIGS. 13–14A, there are shown circuit diagrams illustrating exemplary circuits for implementing the signal analyzer module 50a, and the display panel module 34a. As shown in FIG. 13, the output of converter 14 is connected to three operational-amplifier circuits wired in parallel. Each of the three operational-amplifier circuits compares the voltage output of converter 14 to a different threshold (reference) voltage. The reference voltages may be checked/calibrated using the test voltages mentioned above. The outputs of the three operational-amplifier circuits and the test voltages are separately provided to display panel module 34a. Based on the outputs of the operational-amplifiers in the signal analyzer module 50a, the three LED's on the display panel 34 are selectively illuminated as described above. FIG. 14A also shows the latching circuits for the secondary LED's 42 and 44 of display panel 34 with a reset switch. Circuit location of the power indicator LED 46 and light source failure indicator LED 48 are shown in FIG. 14. Similar circuits can be constructed with the input reference voltages of the operational-amplifiers hooked in series as in a standard light column volt meter.

Although FIGS. 10–14A illustrate a specific circuitry arrangement for implementing the present invention, it will be understood by those skilled in the art that other circuitry arrangements may alternatively be employed.

Figure 15:
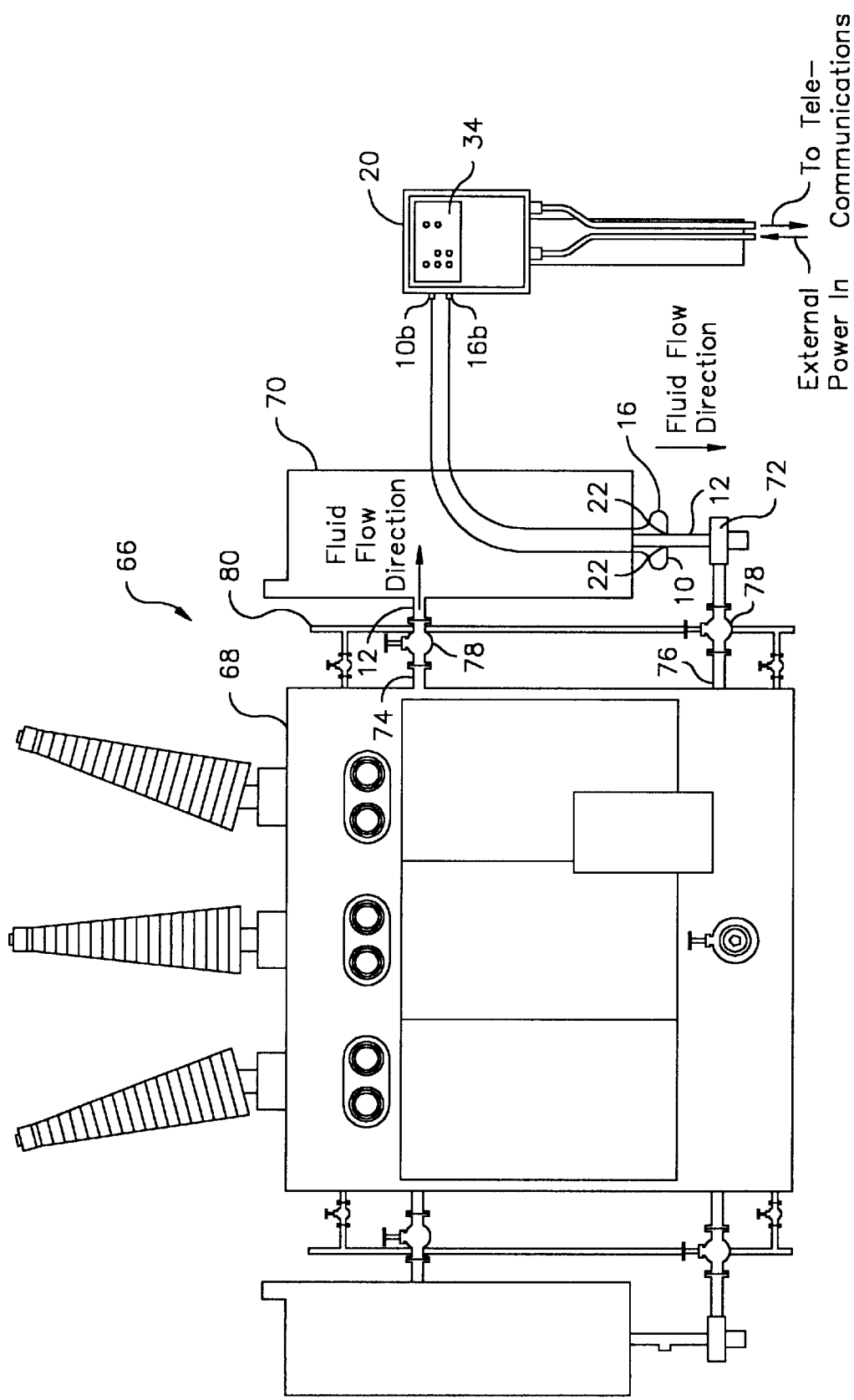
FIG. 15 is a block diagram showing an electrical transformer having an on-line system for continuously monitoring the condition of transformer oil circulating within the transformer, in accordance with a preferred embodiment of the present invention.
Figure 16:
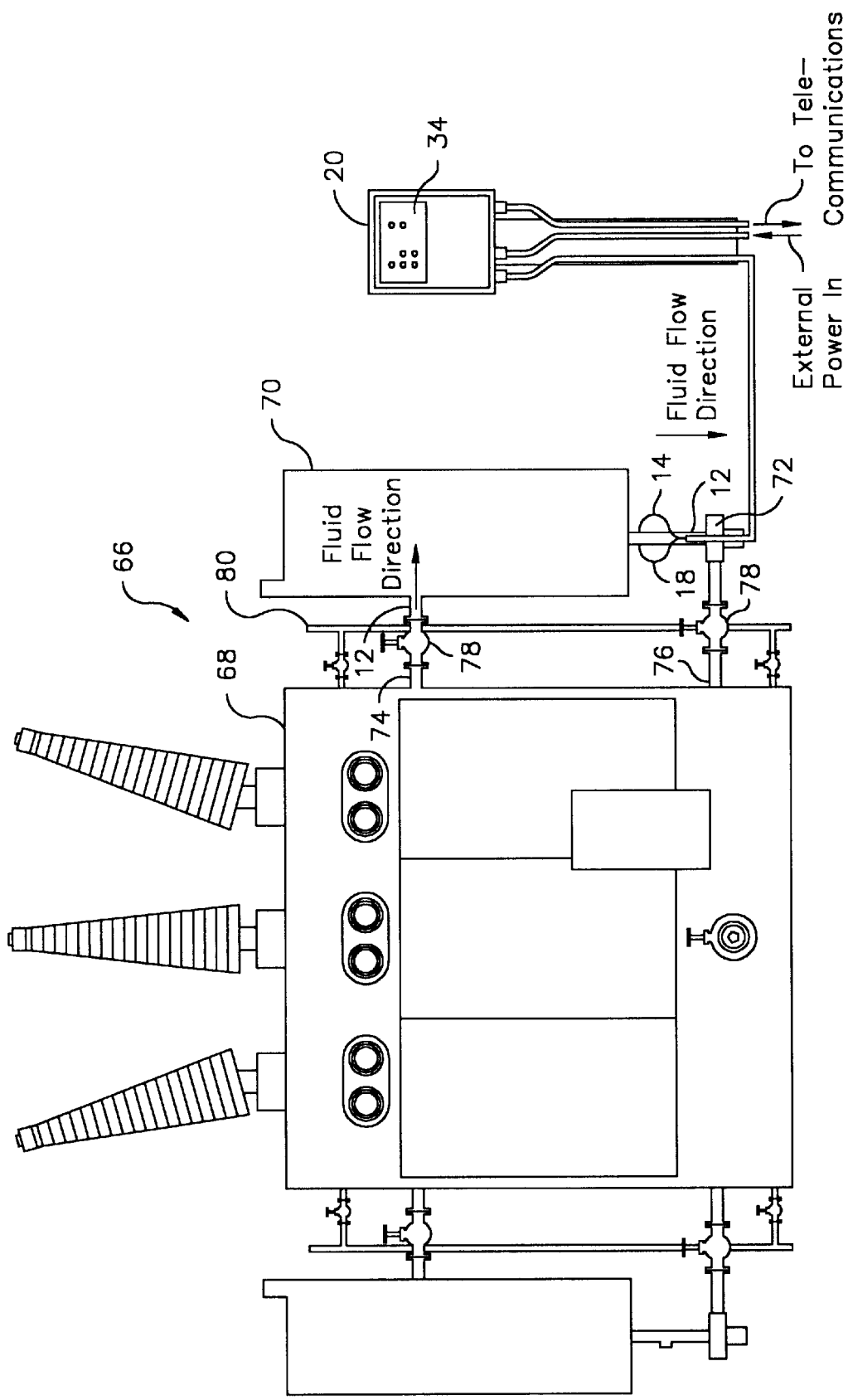
FIG. 16 is a block diagram showing an electrical transformer having an on-line system for continuously monitoring the condition of transformer oil circulating within the transformer, in accordance with an alternative preferred embodiment of the present invention.

In one preferred embodiment for applications used in the electrical utilities, the system is used to determine the condition of transformer insulating fluid used in liquid type transformers 66. This preferred embodiment is shown in FIGS. 15 and 16. Transformer 66 is formed from an outer transformer casing 68 which encloses internal transformer components which vary in design by manufacturer according to power rating, coil design and cooling systems. In a liquid type transformer 66, the transformer windings (shown in FIGS. 17, 18 and 19) are immersed in transformer oil (or liquid insulation) which is also enclosed by transformer casing 68. During operation of transformer 66, the transformer oil continuously circulates around the transformer windings and through an oil/heat exchanger 70. The transformer oil is preferably circulated during operation of the transformer 66 with an oil pump 72. Alternatively, the transformer oil may be circulated through the transformer by convective forces. An oil outlet port 74 is provided for withdrawing oil from within casing 68; oil withdrawn from casing 68 through port 74 is then provided to oil/heat exchanger 70 for cooling. An oil inlet port 76 is provided for recirculating cooled oil (which has passed through oil/heat exchanger 70) back into casing 68. Ports 74, 76 are coupled to oil/heat exchanger 70 by conduit 12. Valves 78 are provided for regulating the flow of the transformer oil through ports 74, 76 and oil/heat exchanger 70. A gravity driven oil level indicator 80 (formed from a clear material) is provided for visually indicating the level of transformer oil within casing 68.

Referring specifically to FIG. 15, placement of optical transmission and acquisition fibers 10 and 16 respectively through optical fiber mounts 22 are shown on conduit 12 between oil/heat exchanger 70 and pump 72. Fibers 10 and 16 are connected to housing 20 with display panel 34 which in this embodiment contains optical source 18 and optical detector 14 (as shown in FIG. 3).

Referring specifically to FIG. 16, optical source 18 and optical detector 14 are connected to conduit 12 between oil/heat exchanger 70 and pump 72 (as shown in FIG. 5). Optical source 18 and optical detector 14 are then electrically connected to housing 20 with display panel 34 (as shown in FIG. 6).

Figure 17:
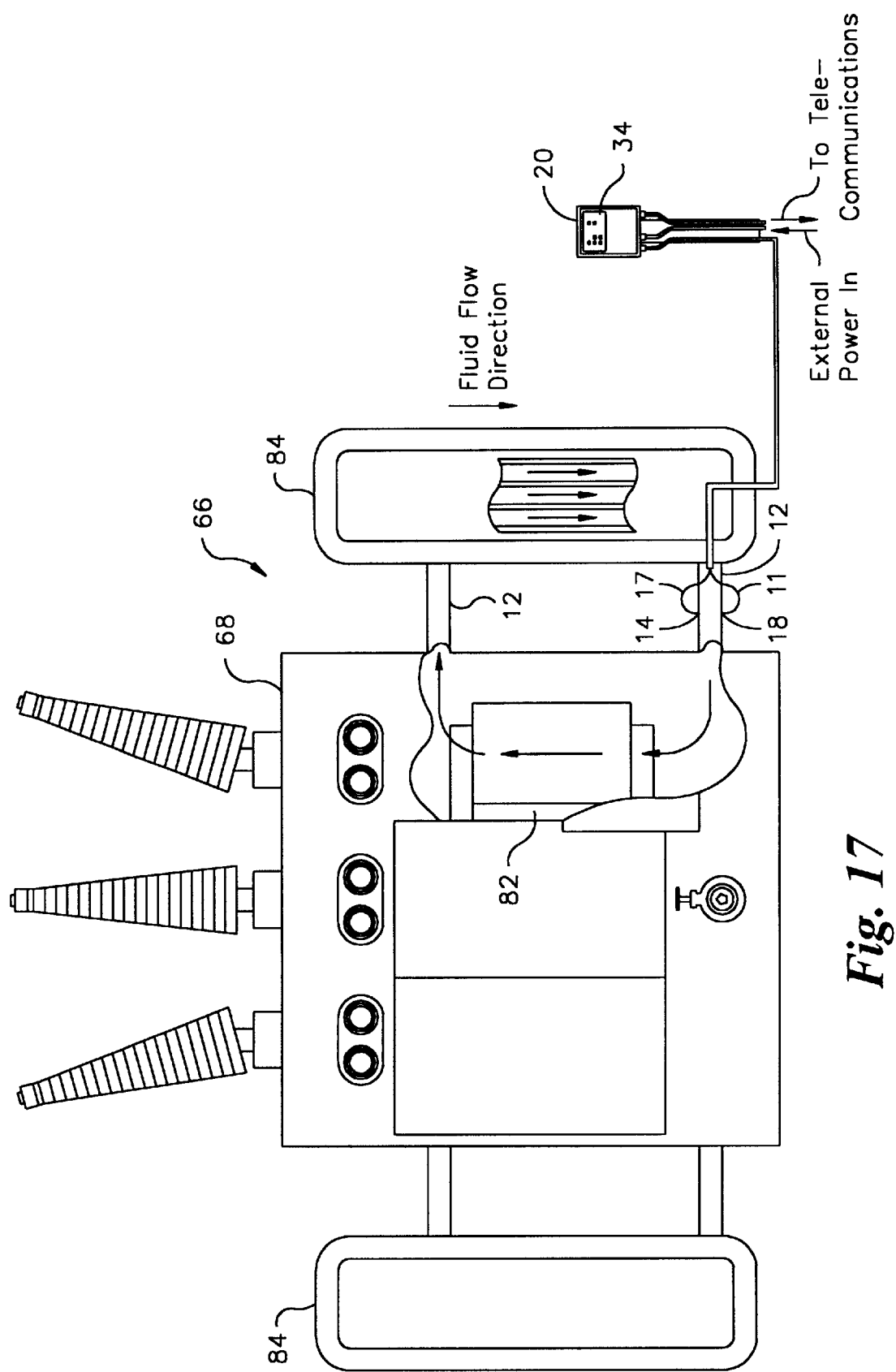
FIGS. 17–19 are block diagrams illustrating various transformers having on-line systems for continuously monitoring the condition of transformer oil circulating therein, in accordance with further alternative embodiments of the present invention.
Figure 18:
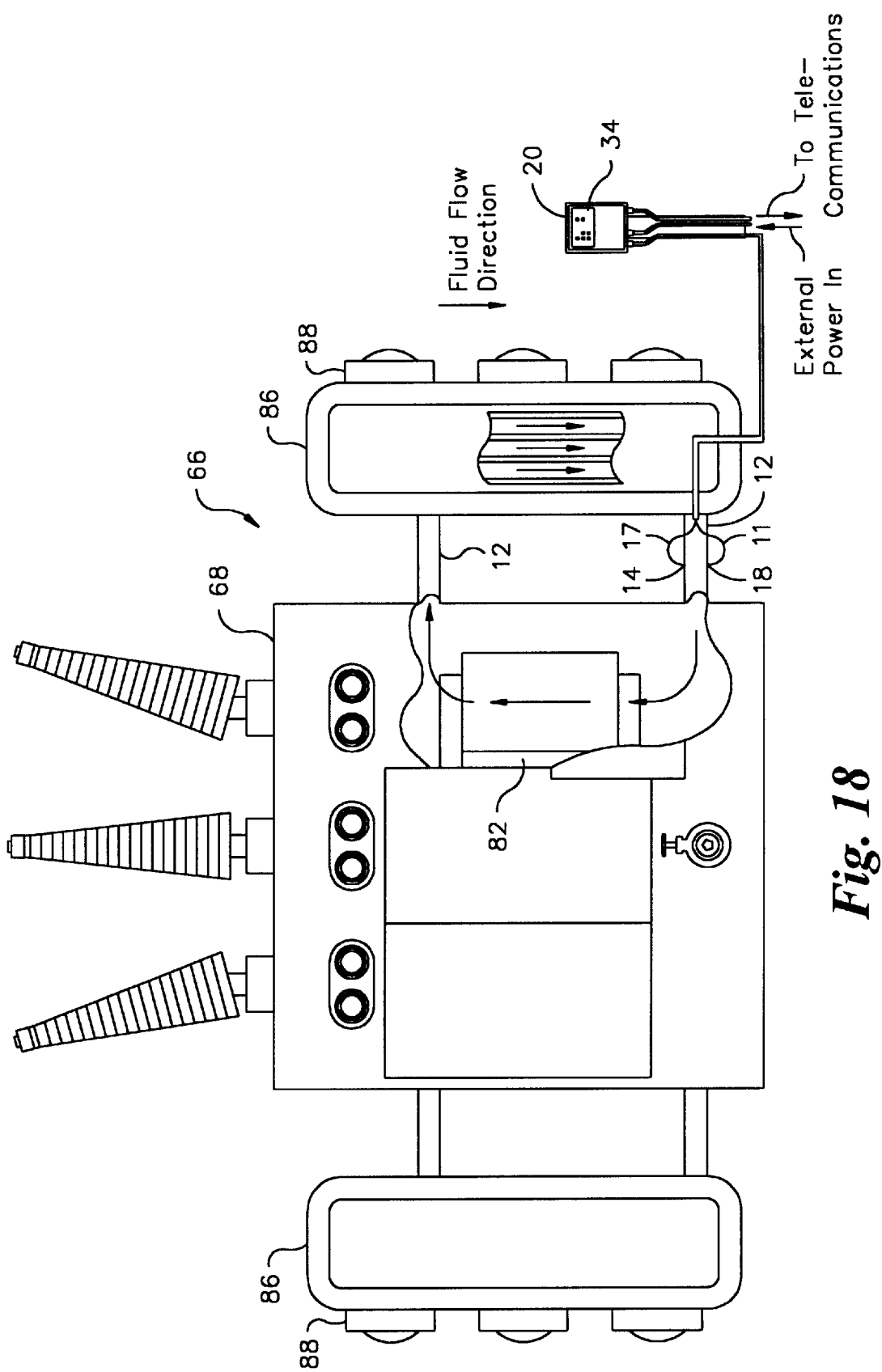
Figure 19:
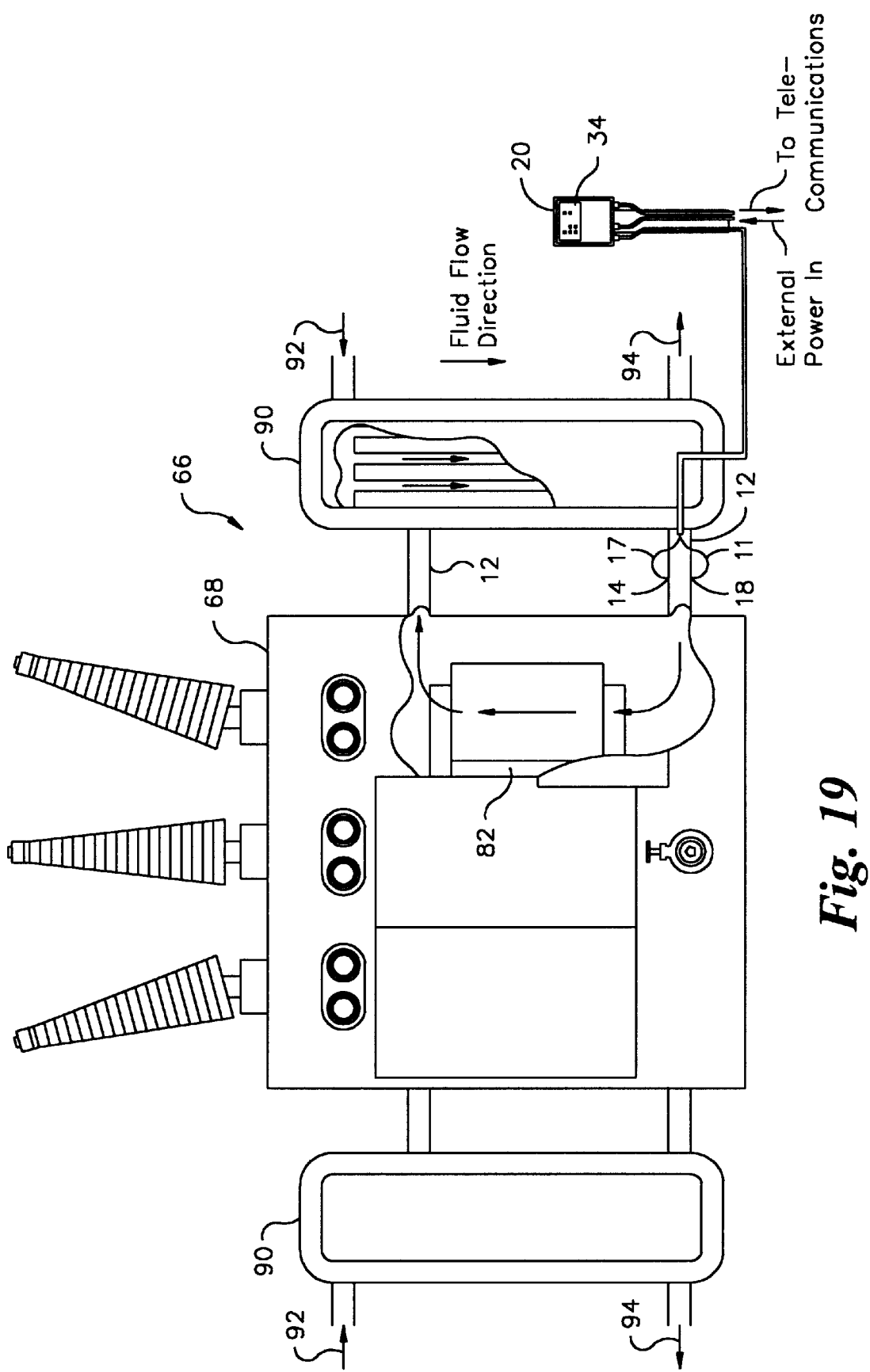

Referring now to FIGS. 17–19, there are shown diagrams illustrating the optical monitoring system of the present invention installed in other types of liquid transformers 66a, 66b, 66c in accordance with alternative preferred embodiments of the present invention. FIGS. 17–19 also show the fluid flow path of the transformer 66 through the transformer windings 82 and associated heat exchangers 84, 86 and 90. FIG. 17 depicts a transformer 66a cooled with a natural convection oil/air heat exchanger 84. FIG. 18 illustrates a transformer 66b cooled with a forced air natural convection oil/air exchanger 86 with external fans 88. FIG. 19 depicts a transformer 66c cooled with an oil/water heat exchanger 90 with cooling water inlet 92 and outlet 94.

Installation of the present invention is independent of specific liquid type transformer designs and is only dependent on adequate spacing for mounting the optical devices. Due to sensitive electronic elements of the electrical circuits, it is often advantageous to locate these circuits an adequate distance from any vibrational source which may effect the calibration settings of the instrument. Selection of the optical materials are dependent upon the application and environment specific to the given fluid circuit in which it is installed. Other devices to which the present invention applies include liquid circuits in automobiles, aircraft and ships.

Figure 20A:
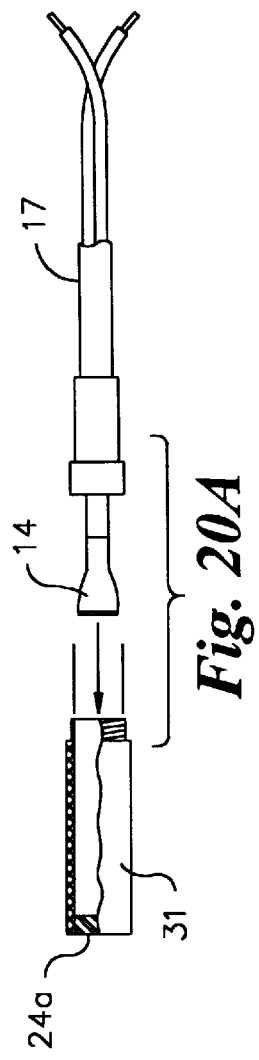
FIGS. 20A, 20B, 20C and 20D are schematic diagrams of optical probes which are sized for insertion into the optical mount shown in FIG. 22, in accordance with an alternative preferred embodiment of the present invention.
Figure 20B:
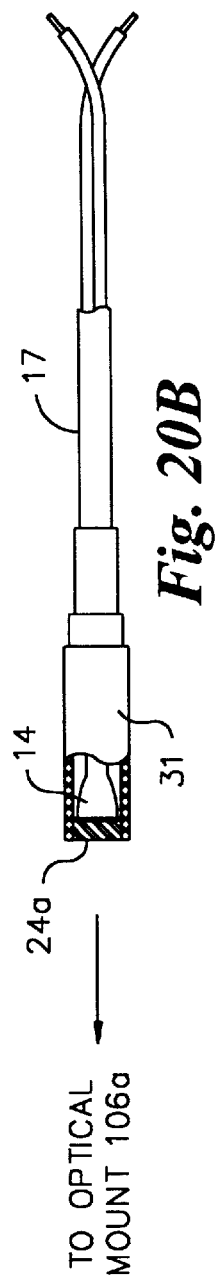
Figure 20C:
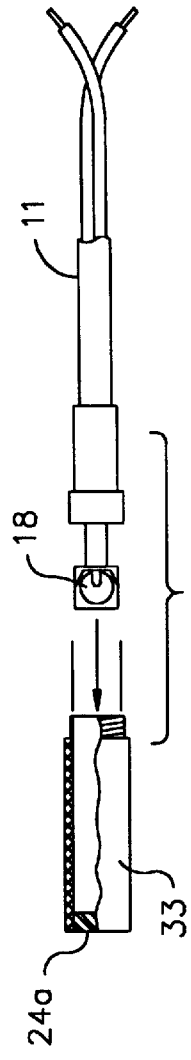
Figure 20D:
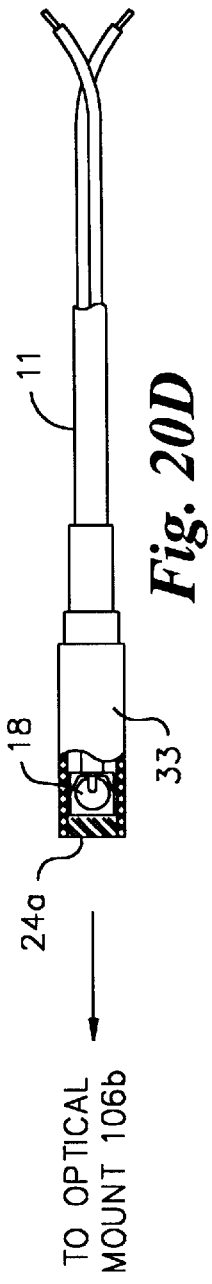

Referring now to FIGS. 20A, 20B, 20C and 20D, there are shown schematic diagrams of optical probes which are sized for insertion into the optical mount 106 shown in FIG. 22, in accordance with an alternative preferred embodiment of the present invention. FIGS. 20A and 20B depict an optical probe which contains an optical detector 14, and FIGS. 20C and 20D depict an optical probe which contains an optical source 18. In the optical probe shown in FIGS. 20A and 20B, wire pair 17 is coupled on one end to optical detector 14, and on an opposite end to circuit board connection 26. Optical detector 14 is disposed within optical detector holder 31 such that the optical reception surface of detector 14 is positioned adjacent to transparent aperture 24a. In the optical probe shown in FIGS. 20C and 20D, a wire pair 11 is coupled on one end to optical source 18, and on an opposite end to circuit board connection 28. Optical source 18 is disposed within optical source holder 33 such that light emitted from source 18 is transmitted through the transparent aperture 24a positioned adjacent to source 18. Holders 31 and 33 are both sized for insertion into an optical mount 106 (shown in FIG. 22).

Figure 21A:
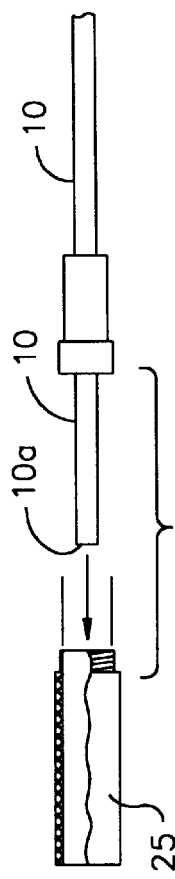
FIGS. 21A, 21B, 21C and 21D are schematic diagrams of optical probes which are sized for insertion into the optical mount shown in FIG. 22, in accordance with an alternative preferred embodiment of the present invention.
Figure 21B:
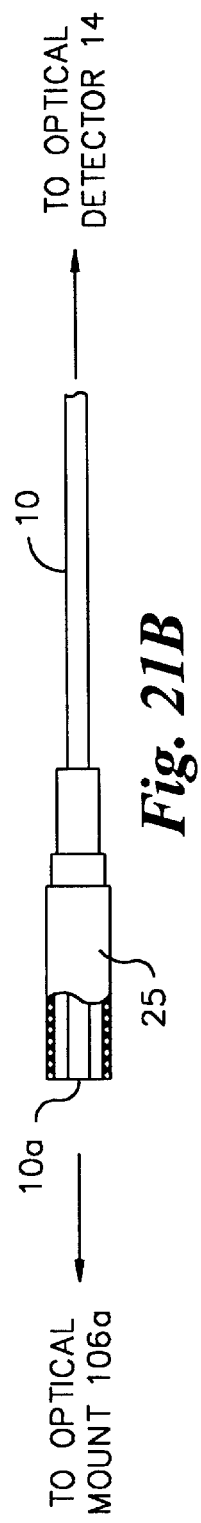
Figure 21C:
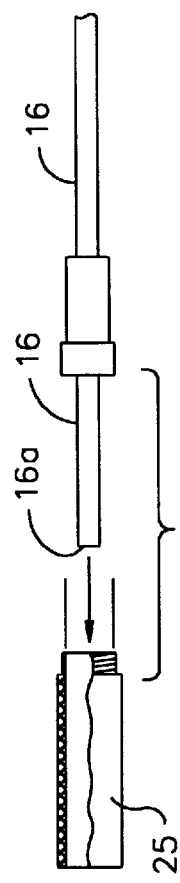
Figure 21D:
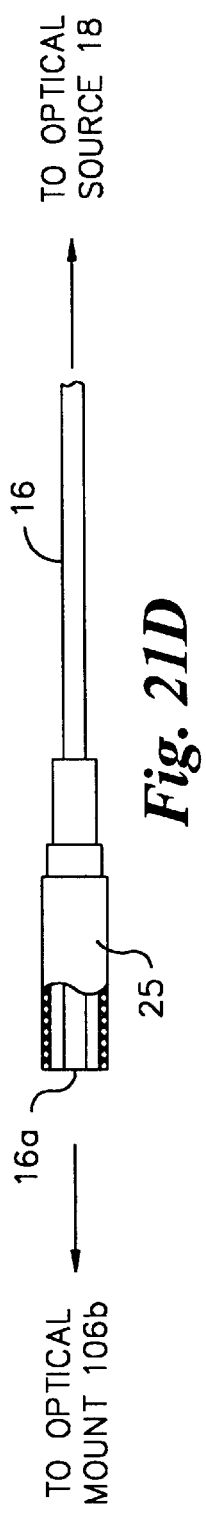

Referring now to FIGS. 21A, 21B, 21C and 21D, there are shown schematic diagrams of optical probes which are sized for insertion into the optical mount 106 shown in FIG. 22, in accordance with a still further alternative preferred embodiment of the present invention. FIGS. 21A and 21B depict an optical probe which is coupled by optical strand 10 to an optical detector 14, and FIGS. 21C and 21D depict an optical probe which is coupled by optical strand 16 to an optical source 18. In the optical probe shown in FIGS. 21A and 21B, end 10a of optical fiber strand 10 is disposed at an end face of holder 25, and in the optical probe shown in FIGS. 21C and 21D, end 16a of optical fiber strand 16 is disposed at an end face of holder 25. Holders 25 are sized for insertion into an optical mount 106 (shown in FIG. 22).

Referring now to FIG. 22, there is shown a schematic diagram of a fluid module 101 for insertion into a fluid circuit for monitoring the condition of fluid flowing within the fluid circuit, in accordance with an alternative embodiment of the present invention. Fluid module 101 is constructed of an optically opaque square tube 110 which is optically sealed with optically opaque end caps 102. Conduit 104 is coupled to each end of square tube 110 by square tube adapters 112. Adapters 112 provide a liquid type seal to each end of an optically transparent tube 108 disposed within square tube 110. Hollow optical mounts 106a, 106b pass through and are attached to square tube 110. Optical mounts 106a, 106b do not break the surface of transparent tube 108, and optical mounts 106a, 106b preferably instead abut the surface of transparent tube 108. In one embodiment, the two probes shown in FIGS. 20A–20D are respectively secured within optical mounts 106a, 106b in order to optically monitor the condition of fluid flowing through module 101. In an alternate embodiment, the two probes shown in FIGS. 21A–21D are respectively secured within optical mounts 106a, 106b in order to optically monitor the condition of fluid flowing through module 101. Although the fluid module shown in FIG. 22 includes only two optical mounts 106a, 106b, it will be understood by those skilled in the art that a fluid module 101 could include further additional optical mounts for attachment of further sensing elements to module 101.

Figure 23:
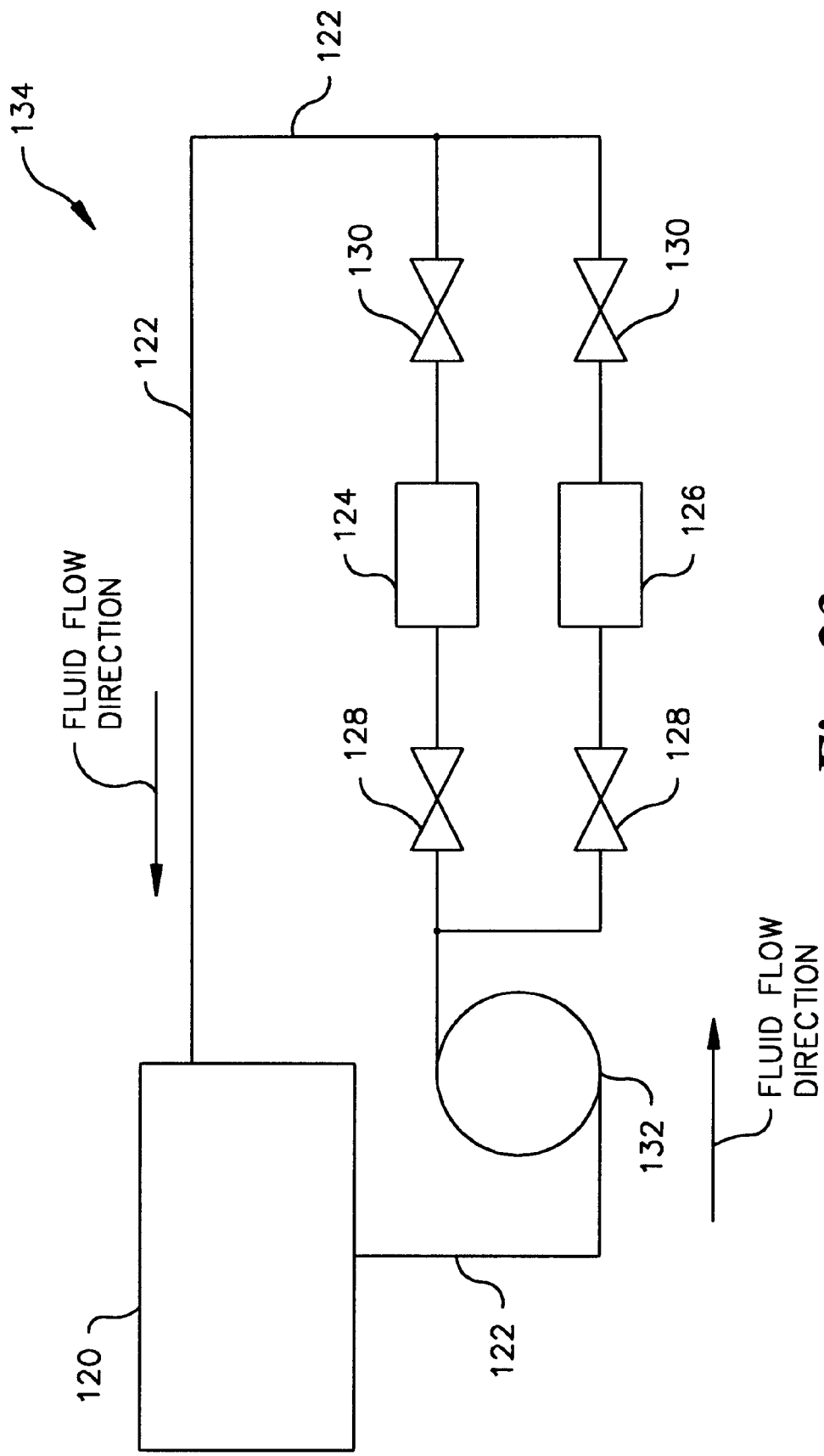
FIG. 23 is a block diagram of a fluid circuit for testing and calibrating the fluid monitoring systems of the present invention.

Referring now to FIG. 23, there is shown a block diagram of a fluid circuit 134 for testing and calibrating the fluid monitoring systems of the present invention. Fluid circuit 134 includes a fluid reservoir 120 which flows to pipe 122 and then into pump 132. Pump 132 discharges into inlet valves 128 whose outlets are connected to fluid modules 124 and 126. Fluid module 124 corresponds to the on-line monitoring system shown in FIGS. 1–6, and fluid module 126 corresponds to an on-line monitoring system which includes the fluid module 101 shown in FIG. 22. The outlets of fluid modules 124 and 126 discharge through outlet valves 130 to return pipe 122. Return pipe 122 is connected back to the fluid reservoir 120 thus completing the fluid circuit loop. Fluid reservoir 120 has the ability to accept foreign fluids or materials to simulate degrading fluid.

Figure 24:
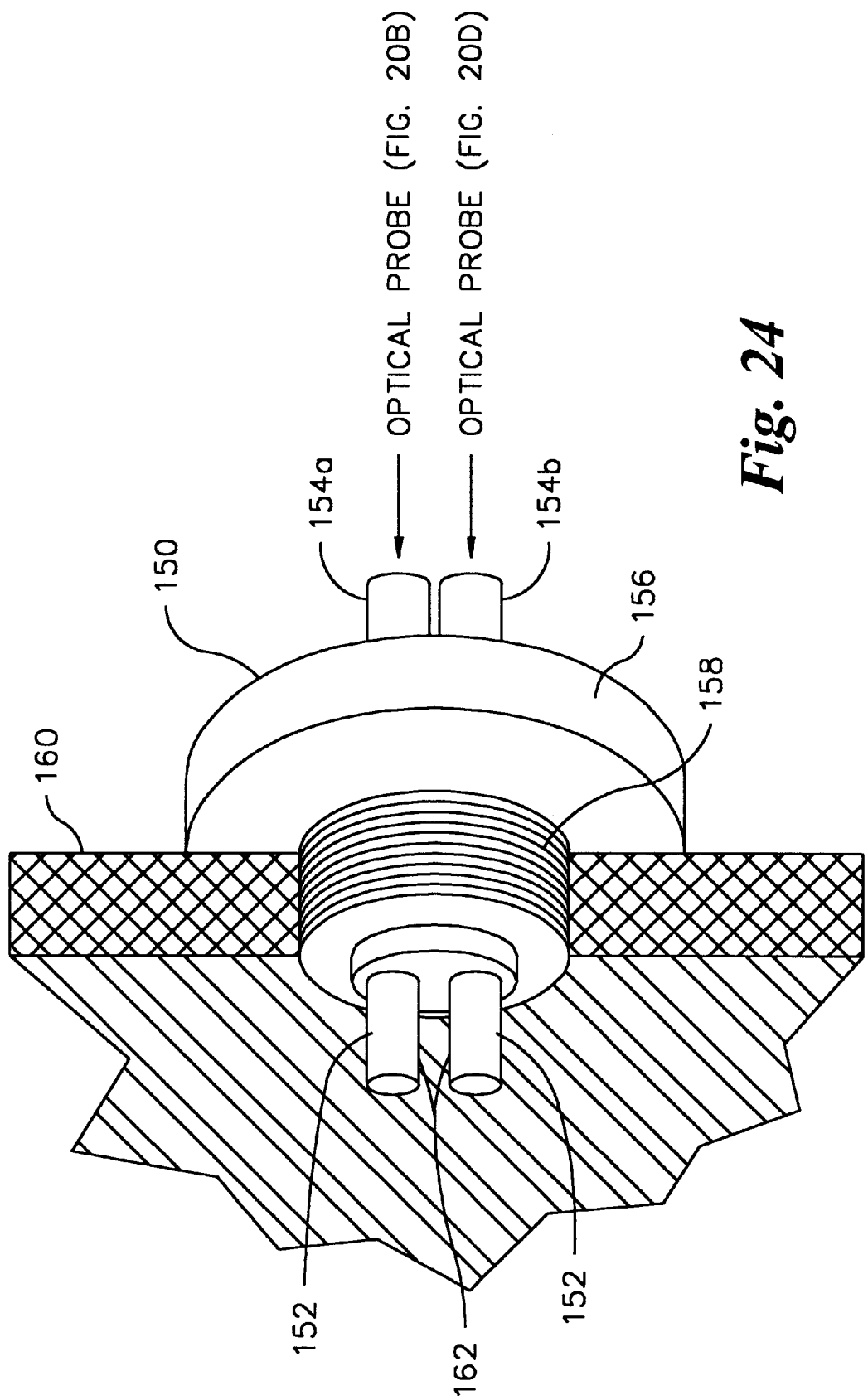
FIG. 24 is a cut-away view of an optical sensor head coupled to an opaque reservoir housing, in accordance with a further alternative embodiment of the present invention.
Figure 25:
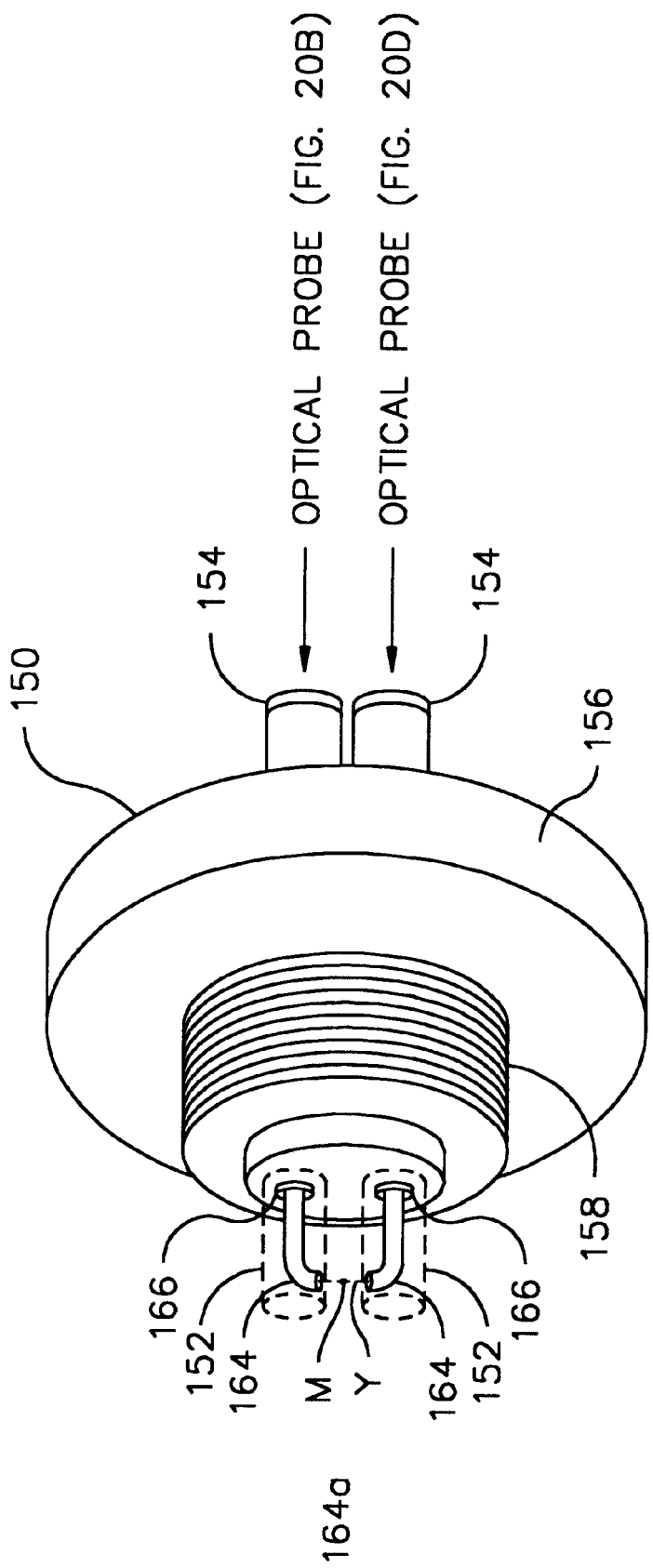
FIG. 25 is a further view of the optical sensor head shown in FIG. 24.

Referring now to FIG. 24, there is shown a cut-away view of an optical sensor head 150 coupled to an opaque reservoir housing 160, in accordance with a further alternative embodiment of the present invention. In this configuration, the optical sensor head 150 is used as a single interface for monitoring fluid in opaque reservoir housing 160. The optical sensor head 150 is constructed with optical probe mounts 154a, 154b mounted on the exterior surface of optical sensor head mounting plate 156. The optical probe mounts 154a, 154b are supplied for receiving and mounting the optical probes depicted in FIGS. 20B and 20D; alternatively, optical probe mounts 154a, 154b may receive and mount the optical probes depicted in FIGS. 21B and 21D. Optical sensor head mounting plate 156 and optical sensor head mounting threads 158 are provided to insure a leak tight interface between the optical sensor head 150 and the opaque reservoir housing 160. Mounted on the interior of optical sensor head 150 are optical conduit housings 152 with transparent optical apertures 162. Each optical aperture 162 is optically connected to an end of an optical probe by an optical conduit 164 (shown in FIG. 25). As shown in FIG. 25, optical conduits 164 are secured to head 150 by mounting threads 166. Optical conduit ends 164a are preferably aligned along a common axis (Y) such that light transmitted from one of optical conduit end 164a may be received through the opposing optical conduit end 164a. Optical conduit housings 152 provide a solid structural boundary between optical elements positioned within the housings 152 and the surrounding liquid environment.

Figure 26:
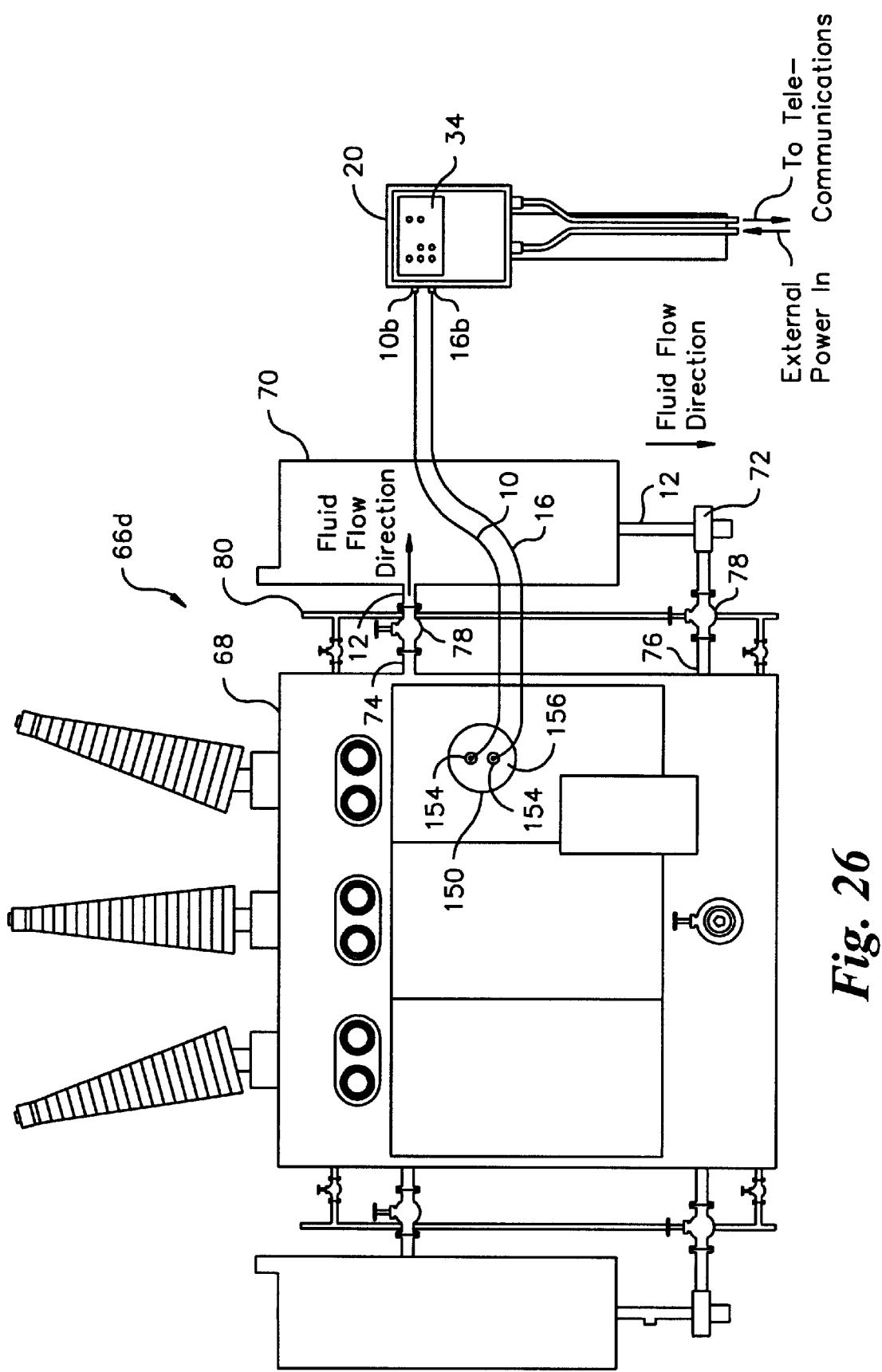
FIG. 26 is a block diagram showing an electrical transformer having an on-line system which uses the optical sensor head shown in FIGS. 24 and 25 for continuously monitoring the condition of transformer oil within the transformer, in accordance with an alternative preferred embodiment of the present invention.

Referring now to FIG. 26, there is shown a block diagram illustrating an electrical transformer 66d having an on-line system which uses the optical sensor head 150 shown in FIGS. 24 and 25 for continuously monitoring the condition of transformer oil within the transformer, in accordance with an alternative preferred embodiment of the present invention. Optical probe mounts 154 are shown exiting optical sensor head mounting plate 156 and connected to the previously described optical fibers 10 and 16. Alternate placement of the optical sensor head 150 is used to provide localized information of the transformer oil (e.g. sludge collecting on the bottom and dissolved gases collecting below the gas blanket in the space provided above the windings 82). With multiple optical sensor heads 150, composite information from multiple transformer locations may be obtained.

Figure 27:
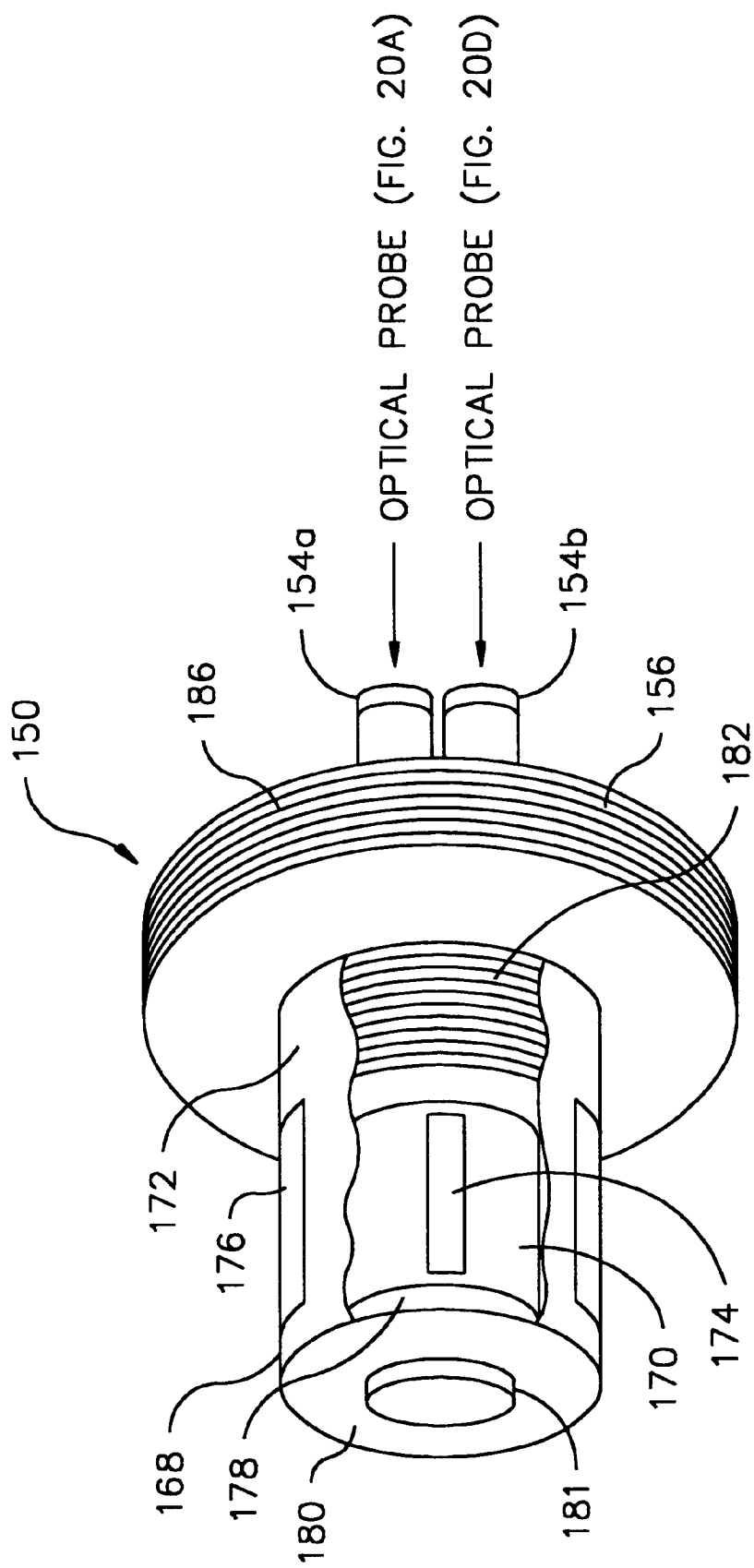
FIG. 27 is a schematic view of an optical sensor head with an optical baffle, in accordance with a further alternative embodiment of the present invention.

Referring now to FIG. 27, there is shown a schematic view of an optical sensor head 150 with an optical baffle 168, in accordance with a further alternative embodiment of the present invention. Optical baffle 168 is provided to block ambient light while still allowing the passage of light within the interior of an inner tube 170 where the optical conduits 164 (not shown in FIG. 27, but shown in FIG. 25) are located. Optical baffle 168 is constructed with concentric tubes consisting of an opaque inner tube 170 with a fluid duct opening 174 and an opaque outer tube 172 with a fluid duct opening 176. The fluid ducts openings 174 and 176 are provided for the passage of a fluid and function to minimize the occurrence of air pockets in the interior of inner tube 170. The inner tube 170 is terminated with an opaque inner tube end cap 178. The outer tube 172 is likewise terminated with an opaque outer tube end cap 180. The outer tube 172 is mounted to the optical sensor head 150 with outer tube mounting threads 182. The inner tube is likewise mounted to the optical sensor head 150 with inner tube mounting threads (not shown). This embodiment of the optical sensor head 150 is preferably provided with external mounting threads 186. Practical uses of this embodiment of optical sensor head 150 include oceanographic studies. In such applications, the sensor head 150 may be fitted with weights and immersed into the ocean at a desired depth. The instrument then reports the clarity of the sea water at this depth in order to assist in a decision as to whether to send either divers or remote cameras to that depth. This embodiment is also easily adaptable for attachment on manned and unmanned submersible vehicles. The associated electronics are also easily attached to the optical sensor head 150 providing a complete self contained apparatus which is submersed in a pressurized containment capsule. The associated electronics would preferably include a telecommunications package that consists of an active sonar telemetry package.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. An apparatus for determining a condition of an electrical transformer formed from windings and a fluid which circulates within said electrical transformer, comprising:
   (A) an optical source for generating light;
   (B) an optical detector for receiving said light;
   (C) a signal analyzer, coupled to said optical detector, for monitoring an output of said optical detector and determining said condition of said electrical transformer in accordance with said output of said optical detector; and
   wherein said windings and said fluid are disposed within a transformer casing, said transformer casing having a fluid input port for receiving said fluid into said transformer casing, and a fluid output port for discharging said fluid from said transforming casing, said apparatus further comprising a transparent conduit in fluid communication with said fluid input port and said fluid output port, said fluid is re-circulated from said fluid output port to said fluid input port via said transparent conduit, said transparent conduit having said re-circulated fluid therethrough being positioned between said optical source and said optical detector.

2. The apparatus of claim 1, wherein said recirculated fluid is transformer oil.

3. The apparatus of claim 1, wherein said transparent conduit is positioned outside of said transformer casing.

4. The apparatus of claim 3, further comprising an indicator panel, coupled to said signal analyzer, for displaying said condition of said electrical transformer.

5. The apparatus of claim 1, said signal analyzer including means for comparing said output of said optical detector to a first threshold value, wherein said condition of said electrical transformer is determined in accordance with whether said output of said optical detector is below said first threshold value.

6. The apparatus of claim 5, said signal analyzer including means for comparing said output of said optical detector to a second threshold value, wherein said condition of said electrical transformer is determined in accordance with whether said output of said optical detector is below said second threshold value.

7. The apparatus of claim 6, wherein said condition determined by said signal analyzer corresponds to a transformer state selected from the group consisting of a normal state, a maintenance state, and a danger state.

8. The apparatus of claim 7, wherein said signal analyzer includes:
   (1) means for selecting said danger state as said condition of said electrical transformer if said output of said optical detector is above said first and second threshold values;
   (2) means for selecting said maintenance state as said condition of said electrical transformer if said output of said optical detector is above said first threshold value and below said second threshold value; and
   (3) means for selecting said normal state as said condition of said electrical transformer if said output of said optical detector is below said first and second threshold values, said second threshold value being higher than said first threshold value.

9. The apparatus of claim 1, wherein said optical source is an incandescent lamp.

10. The apparatus of claim 1, wherein said optical source is a laser light source.

11. The apparatus of claim 1, wherein said optical source is a UV light source.

12. A method for determining a condition of an electrical transformer formed from windings and a fluid which circulates within said electrical transformer, comprising the steps of:
    (A) generating light with an optical source;
    (B) receiving said light with an optical detector;
    (C) monitoring, with a signal analyzer, an output of said optical detector and determining said condition of said electrical transformer in accordance with said output of said optical detector; and
    wherein said windings and said fluid are disposed within a transformer casing, said transformer casing having a fluid input port for receiving said fluid into said transformer casing, and a fluid output port for discharging said fluid from said transforming casing, said method further comprising the step of:
    (D) re-circulating said fluid from said fluid output port to said fluid input port via a transparent conduit in fluid communication with said fluid input port and said fluid output port, said transparent conduit having said re-circulated fluid therethrough being positioned between said optical source and said optical detector.

13. The method of claim 12, wherein said fluid is transformer oil.

14. The method of claim 12, wherein steps (A)–(D) are performed while said electrical transformer is on-line.

15. The method of claim 14, further comprising the step of displaying said condition of said electrical transformer on an indicator panel coupled to said signal processor.

16. The method of claim 14, wherein step (C) further comprises the steps of comparing said output of said optical detector to a first threshold value, and determining said condition of said electrical transformer in accordance with whether said output of said optical detector is below said first threshold value.

17. The method of claim 16, wherein step (C) further comprises the steps of comparing said output of said optical detector to a second threshold value, and determining said condition of said electrical transformer in accordance with whether said output of said optical detector is below said second threshold value.

18. The method of claim 17, wherein said condition determined in step (C) corresponds to a transformer state selected from the group consisting of a normal state, a maintenance state, and a danger state.

19. The method of claim 18, wherein step (C) further comprises the steps of:
   (1) selecting said danger state as said condition of said electrical transformer if said output of said optical detector is above said first and second threshold values;
   (2) selecting said maintenance state as said condition of said electrical transformer if said output of said optical detector is above said first threshold value and below said second threshold value; and
   (3) selecting said normal state as said condition of said electrical transformer if said output of said optical detector is below said first and second threshold values, said second threshold value being higher than said first threshold value.

20. The method of claim 12, wherein said optical source is an incandescent lamp.

21. The method of claim 12, wherein said optical source is a laser light source.

22. The method of claim 12, wherein said optical source is a UV light source.

* * * * *